US007141603B2

(12) United States Patent
McMorris et al.

(10) Patent No.: US 7,141,603 B2
(45) Date of Patent: Nov. 28, 2006

(54) ANTITUMOR AGENTS

(75) Inventors: Trevor C. McMorris, La Jolla, CA (US); Michael J. Kelner, La Jolla, CA (US)

(73) Assignee: The Regents of The University California, Oakland, CA (US)

( * ) Notice: Subject to any disclaimer, the term of this patent is extended or adjusted under 35 U.S.C. 154(b) by 0 days.

(21) Appl. No.: 11/151,013

(22) Filed: Jun. 13, 2005

(65) Prior Publication Data

US 2005/0250675 A1 Nov. 10, 2005

Related U.S. Application Data

(60) Division of application No. 10/413,449, filed on Apr. 14, 2003, now Pat. No. 6,908,918, which is a continuation of application No. 09/641,191, filed on Aug. 17, 2000, now Pat. No. 6,548,679, which is a continuation of application No. PCT/US99/03660, filed on Feb. 19, 1999.

(51) Int. Cl.
*A61K 31/335* (2006.01)
*C07D 317/72* (2006.01)
*C07C 49/453* (2006.01)

(52) U.S. Cl. .................. 514/462; 549/339; 568/373
(58) Field of Classification Search ................ 568/373; 514/462; 549/339
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,612,302 A | 9/1986 | Szabo et al. | |
| 4,684,620 A | 8/1987 | Hruby et al. | |
| 4,820,508 A | 4/1989 | Wortzman | |
| 4,853,371 A | 8/1989 | Coy et al. | |
| 4,938,949 A | 7/1990 | Borch et al. | |
| 4,992,478 A | 2/1991 | Geria | |
| 5,387,578 A | 2/1995 | Angelucci et al. | |
| 5,439,936 A | 8/1995 | Kelner et al. | |
| 5,439,942 A | 8/1995 | Kelner et al. | |
| 5,523,490 A | 6/1996 | Kelner et al. | |
| 5,563,176 A | 10/1996 | Kelner et al. | |
| 5,723,632 A | 3/1998 | McMorris | |
| 5,932,553 A | 8/1999 | McMorris et al. | |
| 6,025,328 A | 2/2000 | McMorris et al. | |

FOREIGN PATENT DOCUMENTS

| | | |
|---|---|---|
| JP | 62-234040 | 10/1987 |
| WO | WO-91/04754 | 4/1991 |
| WO | WO-94/18151 | 8/1994 |
| WO | WO-94/25013 | 11/1994 |
| WO | WO-96/34005 | 10/1996 |
| WO | WO-97/03995 | 2/1997 |
| WO | WO-98/03458 | 1/1998 |

OTHER PUBLICATIONS

Anchel, Marjorie, et al., "Antibiotic Substances From Basidiomycetes. VII. Clitocybe Illudens", *Proceedings of the National Academy of Sciences*, 36 (5), (1950),300-305.
Anchel, M., et al., "The Biogenesis of Illudins S and M in Clitocybe Illudens", *Phytochemistry*, 9(11), (Nov. 1970),2339-2343.
Arap, Wadih, et al., "Cancer Treatment by Targeted Drug Delivery to Tumor Vasculature in a Mouse Model", *Science*, 279(5349), (Jan. 16, 1998),377-380.
Brandsteterova, E., et al., "HPLC Analysis of Novel Anti-Cancer Agents-Illudens and Their Analogs", *Journal of Liquid Chromatography*, 16 (1), (1993),pp. 115-125.
Brandsteterova, E., et al., "HPLC Determination of a New Anticancer Agent (Acylfulvene) in Serum", *Neoplasma*, 39 (6), (1992),pp. 369-373.
Burres, N. S., et al., "Antitumor Activity and Mechanism of Action of the Novel Marine Natural Products Mycalamide-A and -B and Onnamide", *Cancer Research*, 49, (Jun. 1989),2935-2940.
Curtis, Erin A., et al., "An Efficient Dipolar-Cycloaddition Route to the Plerosin Family of Sesquiterpenes", *Tetrahedron Letters*, 36 (12), (Mar. 1995),pp. 1989-1992.
Dillman, R. O., et al., "Athymic Mouse Model of a Human T-Cell Tumor", *Cancer Research*, 45, (Nov. 1985),pp. 5632-5636.
Eva, K. M., et al., "An Efficient Synthesis of Pterosin C and Other Plerosins", *Canadian Journal of Chemistry*, 62 (10), (Oct. 1984),pp. 1945-1953.

(Continued)

*Primary Examiner*—Taofiq Solola
(74) *Attorney, Agent, or Firm*—Schwegman, Lundberg, Woessner & Kluth P.A.

(57) ABSTRACT

The present invention provides compounds of general formula I or II:

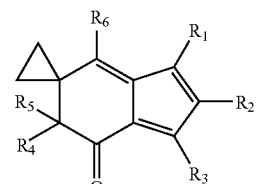

I

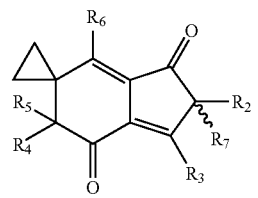

II wherein $R_1$, $R_2$, $R_3$, $R_4$, $R_5$, $R_6$, and $R_7$ have any of the values defined in the specification, and pharmaceutically acceptable salts thereof, as well as pharmaceutical compositions comprising compounds of formula I or II, intermediates and processes useful for preparing compounds of formula I or II, and methods comprising inhibiting tumor growth or treating cancer by administering one or more compounds of formula I or II.

20 Claims, 3 Drawing Sheets

OTHER PUBLICATIONS

Fassina, G., "Oriented Immobilization of Peptide Ligands on Solid Supports", *J. Chromatogr.*, 591, Abstract Only, Obtained from Chemical Abstracts, Accession No. 1992:174737,(1992), 1 p.

French, A. L., et al., "Poisoning with the North American Jack O' Lantern Mushroom", *Clinical Toxicology*, 26 (1 & 2), (1988),pp. 81-88.

Giovanella, B. C., et al., "Correlation Between Response to Chemotherapy of Human Tumors in Patients and in Nude Mice", *Cancer*, 52, (1983),pp. 1146-1152.

Giovanella, B. C., et al., "DNA Topoisomerase I-Targeted Chemotherapy of Human Colon Cancer in Xenografts", *Science*, 246 (4933), (Nov. 24, 1989),pp. 1046-1048.

Goldin, A., et al., "Current Results of the Screening Program at the Division of Cancer treatment, National Cancer Institute", *Europ. J. Cancer*, 17, (1981),pp. 129-142.

Goldin, A., et al., "Historical Development and Current Strategy of the National Cancer Institute Drug Development Program", *In: Methods in Cancer Research, vol. XVI, Cancer Drug Development Part A, Chapter V*, Academic Press, Inc., New York,(1979),pp. 165-245.

Greene, T. W., *Protective Groups in Organic Synthesis, Chapters 4, 5 & 6*, John Wiley & Sons, Inc., New York,(1981),pp. 114-217.

Hanson, J. R., et al., "Studies in Terpenoid Biosynthesis. Part XV. Biosynthesis. Part XV. Biosynthesis of the Sesquiterpenoid Illuden M", *Journal of the Chemical Society*, Perkin Transactions I,(1976),876-880.

Hara, M., et al., "6-Deoxyilludin M, a New Antitumor Antibiotic: Fermentation, Isolation and Structural Identification", *The Journal of Antibiotics*, 40, (Nov. 1987),pp. 1643-1646.

Harttig, U., et al., "Leaianafulvene, a Sesquiterpenoid Fulvene Derivative from Cultures of Mycena Leaiana", *Phytochemistry*, 29 (12), (1990),pp. 3942-3944.

Hirono, I., "Reproduction of Acute Bracken Poisoning in a Calf with Ptaquiloside, a Bracken Constituent", *The Veterinary Record*, 115 (15), (Oct. 1984),pp. 375-378.

Inoue, K., et al., "Antitumor Efficacy of Seventeen Anticancer Drugs in Human Breast Cancer Xenograft (MX-1) Transplanted in Nude Mice", *Cancer Chemother. Pharamacol.*, 10, (1983),pp. 182-186.

Ito, R. K., et al., "Biocompatible Substances with Thromboresistance", U.S. Patent No. 5,019,393, Abstract Only, Obtained from Chemical Abstracts, Accession No. 1991:499399,(May 28, 1991), 1 p.

Kawato, Y., et al., "Antitumor Activity of a Camptothecin Derivative, CPT-11, Against Human Tumor Xenografts in Nude Mice", *Cancer Chemother. Pharmacol.*, 28, (1991),pp. 192-198.

Kelner, M. J., et al., "In Vitro and In Vivo Studies on the Anticancer Activity of Dehydroilluden M", *Anticancer Research*, 15, (1995),pp. 873-878.

Kelner, M. J., et al., "Nonresponsiveness of the Metastatic Human Lung Carcinoma MV522 Xenograft to Conventional Anticancer Agents", *Anticancer Research*, 15, (1995),pp. 867-872.

Kelner, M. J., et al., "Preclinical Evaluation of Illudens as Anticancer Agents", *Cancer Research*, 47, (1987),pp. 3186-3189.

Kelner, M. J., et al., "Preclinical Evaluation of Illudens as Anticancer Agents: Basis for Selective Cytotoxicity", *J. Natl. Cancer Inst.*, 82 (19), (1987),pp. 1562-1565.

Lu, Jianliang, et al., "An expeditious synthesis of the potent antitumor agent, (+)-hydroxymethylacylfulvene using an allenic Paulson-Khand type cycloaddition", *American Chemical Society, Division of Organic Chemistry Abstracts*, 217th ACS National Meeting in Anaheim, CA,(Mar. 21-25, 1999), 1 p.

Matsumoto, Takeshi, et al., "An Alternative Synthesis of Illudin M", *Tetrahedron Letters*, 14, (Mar. 1970),pp. 1171-1174.

Matsumoto, T., et al., "Synthesis of Illudin S", *Tetrahedron Letters*, 23, (May 1971),pp. 2049-2052.

McMorris, T. C., et al., "(Hydroxymethyl) Acyfulvene: An Illuden Derivative with Superior Antitumor Properties", *Journal of Natural Products*, 59 (9), (Sep. 1996),896-899.

McMorris, T. C., et al., "(Hydroxymethyl)acylfulvene: An Illudin Derivative with Superior Antitumor Properties", *Chemical Abstracts*, abstract No. 196032, vol. 125, No. 15,(Oct. 7, 1996).

McMorris, T. C., et al., "Acylfulvenes, a New Class of Potent Antitumor Agents", *Experientia*, 52 (1), (Apr. 21, 1995),pp. 75-80.

McMorris, Trevor C., et al., "An Acetal Derivative of Illudin S with Improved Antitumor Activity", *Tetrahedron letters*, 38 (10), (1997),pp. 1697-1698.

McMorris, Trevor C., et al., "Design and Synthesis of Antitumor Acylfulvenes", *The Journal of Organic Chemistry*, 62 (9), (1997),pp. 3015-3018.

McMorris, T. C., et al., "Fungal Metabolites. The Structures of the Novel Sesquiterpenoids Illudin -S and -M", *J. of Amer. Chem. Soc.*, 87 (7), (1965),pp. 1594-1600.

McMorris, T. C., et al., "Metabolism of Antitumor Acylfulvene by Rat Liver Cytosol", *Biochemical Pharmacology*, 57, (1999),pp. 83-88.

McMorris, T. C., et al., "On the Mechanism of Toxicity of Illudens: The Role of Glutathione", *Chemical Research Toxicology*, 3 (6), (Nov./Dec. 1990).pp. 574-579.

McMorris, T. C., et al., "Reaction of Antitumor Hydroxymethylacylfulvene (HMAF) with Thiols", *Tetrahedron*, 53 (43), (1997),pp. 14579-14590.

McMorris, T. C., et al., "Structure and reactivity of Illudens", *Tetrahedron*, 45 (17), (1989),pp. 5433-5440.

McMorris, T. C., et al., "Structure-Activity Relationships of Illudens: Analogs with Improved Therapeutic Index", *Journal of Organic Chemistry*, 57 (25), (Dec. 4, 1992),pp. 6876-6883.

McMorris, Trevor C., "Total Synthesis of hydroxymethylacylfulvene, an antitumour derivative of Illudin S", *Chem. Commun.*, (1997),pp. 315-316.

Padwa, Albert, et al., "An approach toward the Illudin family of sesquiterpenes using the tandem cyclization-cycloaddition reaction of rhodium carbenoids", 62 (5), (Mar. 7, 1997),pp. 1317-1325.

Padwa, Albert, et al., "Generation and Cycloaddition behavior of spirocyclic carbonyl ylides. Application to the synthesis of the Pterosin Family of Sequiterpenes", 61 (1), (Jan. 12, 1996),pp. 73-81.

Padwa, Albert, et al., "Synthetic studies toward Illudins and Ptaguilosin. A Highly Convergent approach via the dipolar cycloaddition of carbonyl ylides", *The Journal of the American Chemical Society*, 116, (1994),pp. 2667-2668.

Schabel, F. M., et al., "Testing Therapeutic Hypotheses in Mice and Man:Observations on the Therapeutic Activity Against Advanced Solid Tumors of Mice Treated with Anticancer Drugs that Have Demonstrated or Potential Clinical Utility for Treatment of Advanced Solid Tumors of Man", *In:Methods in Cancer Research, vol. XVII, Cancer Drug Development Part B, Chapter 1*, Academic Press, Inc.,(1979),pp. 3-50.

Shimomura, O., "The Role of Superoxide Dismutase in Regulating the Light Emission of Luminescent Fungi", *The Journal of Experimental Botany*, 43 (256), (Nov. 1992),pp. 1519-1525.

Shinozawa, S., et al., "The Antitumor Effect of Illudin S (Lampterol) Entrapped in Liposome for Mice Inolculated with Ehrlich Ascites Tumor Cells", *Chemical Abstracts*, 90 (25), Abstract No. 197682m,(Jun. 18, 1979), 1 p.

Steel, G. G., et al., "The Response to Chemotherapy of a Variety of Human Tumor Xenografts", *Br. J. Cancer*, 47, (1983),pp. 001-013.

Tanaka, K., et al., "Metabolism by Rat Liver Cytosol of Illuden S, a Toxic Substance of *Lampteromyces japonicus*. II. Characterization of Illuden S-Metabolizing Enzyme", *Xenobiotica*, 22 (1),, (1992),pp. 33-39.

Tanaka, K., et al., "Metabolism of Illuden S, a Toxic Principle of *Lampteromyces japonicus*, by Rat Liver. I. Isolation and Identification of Cyclopropane Ring-Cleavage Metabolites", *Xenobiotica*, 20 (7), (1990),pp. 671-681.

Tanaka, Ken, et al., "Michael-type addition of Illudin S, a toxic substance from *Lampteromyces japonicus* with Cysteine and Cysteine-containing peptides in vitro", *Chem. Pharm. Bull.*, vol. 44, No. 2, (1996).pp. 273-279.

Varki, N. M., et al., "Cloned Low Metastic Variants from Human Lung Carcinoma Metastases", *Anticancer Research*, 10, (1990),pp. 637-644.

Vendetti, J. M., et al., "Current NCI Preclinical Antitumor Screening in Vivo: Results of Tumor Panel Screening, 1976-1982, and Future Directions", *Advances in Pharmacology and Chemotherapy*, 20, (1984),pp. 1-20.

Venditti, J. M., "The National Cancer Institute Antitumor Drug Discovery Program, Current and Future Perspectives: A Commentary", *Cancer Treatment Reports*, 67 (9), (Sep. 1983),pp. 767-772.

Walser, J., et al., "Mode of Action of Illuden S", *Antimicrobial Agents and Chemotherapy*, 3 (3), (Mar. 1973),pp. 357-363.

Weinreb, S. M., "Fulvenes Derived from Illuden S", *Tetrahedron Letters*, 38, (Sep. 1971),pp. 3489-3491.

Wilbraham, *In: Organic and Biological Chemistry*, (1984),p. 222.

ANTITUMOR AGENTS

CROSS-REFERENCE TO RELATED APPLICATIONS

This application is a divisional of application Ser. No. 10/413,449, filed Apr. 14, 2003, now U.S. Pat. No. 6,908,918, which is a continuation of application Ser. No. 09/641,191, filed Aug. 17, 2000, issued as U.S. Pat. No. 6,548,679, on Apr. 15, 2003, which is a continuation of International Patent Application No. PCT/US99/03660, filed on Feb. 19, 1999, which claims priority to U.S. Ser. No. 09/026,633, filed on Feb. 20, 1998, now issued as U.S. Pat. No. 6,025,328, all of which are incorporated herein by reference.

BACKGROUND OF THE INVENTION

A listing of human cancers for which chemotherapy has exerted a predominant role in increasing life span, approaching normal life expectancy, includes Burkitt's lymphoma, acute lymphocytic leukemia and Hodgkin's disease, along with about 10–15 other tumor types. For example, see A. Golden et al., *Eur J. Cancer*, 17, 129 (1981) (Table 1). While the cure rate of these cancers illustrates the level of success of screening systems in selecting antitumor agents that are effective in man, these responsive tumors represent only a small fraction of the various types of cancer and, notably, there are relatively few drugs highly active against solid tumors such as ovarian cancer, breast cancer, lung cancer and the like. Such drugs include cyclophosphamide, adriamycin, 5-FU, hexamethylmelamine and the like. Thus, patients with many types of malignancies remain at significant risk for relapse and mortality.

After relapse, some patients can be reinduced into remission with their initial treatment regimen. However, higher doses of the initial chemotherapeutic agent or the use of additional agents are frequently required, indicating the development of at least partial drug resistance. Recent evidence indicates drug resistance can develop simultaneously to several agents, including ones to which the patient was not exposed. The development of multiple-drug resistant (mdr) tumors may be a function of tumor mass and constitutes a major cause of treatment failure. To overcome this drug resistance, high-dose chemotherapy with or without radiation and allogenic or autologous bone marrow transplantation can be employed. The high-dose chemotherapy may employ the original drug(s) or be altered to include additional agents. The development of new drugs, non-cross resistant with mdr phenotypes, is required to further the curative potential of current regimens and to facilitate curative interventions in previously treated patients.

The in vitro anti-tumor activity of a novel class of natural products called illudins has been examined by Kelner, M. et al., *Cancer Res.*, 47, 3186 (1987). Illudin M was purified and submitted for evaluation to the National Cancer Institute Division of Cancer Treatment (NCI DCT) in vivo drug screening program. Illudin M significantly increased the life span of rats with Dunning leukemia, but had a low therapeutic index in solid tumor systems. The extreme toxicity of illudins has prevented any applications in human tumor therapy. Recently, synthetic analogs of the illudins have been developed which exhibit promising antitumor activity, including those analogs disclosed in U.S. Pat. Nos. 5,439,936 and 5,523,490.

However, despite these developments, there exists a continuing need for chemotherapeutic agents which inhibit tumor growth, especially solid tumor growth, and which have an adequate therapeutic index to be effective for in vivo treatment.

SUMMARY OF THE INVENTION

The invention provides a compound of formula I:

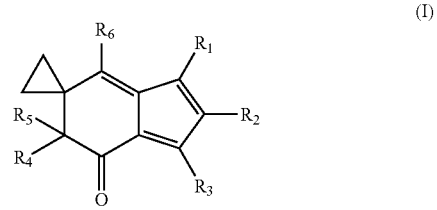

(I)

wherein
- $R_1$ is hydrogen, hydroxy, mercapto, amino, halo, carboxy, nitro, or —$(CH_2)_n$—(X)—(Y);
- n is 0 to 4;
- X is oxy (—O—), thio (—S—), —N($R_a$)—, or absent;
- Y is ($C_3$–$C_6$)cycloalkyl, aryl, heteroaryl, a saccharide, an amino acid, a peptide, or a 1 to 15 membered branched or unbranched carbon chain optionally comprising 1, 2, or 3 non-peroxide oxy, thio, or —N($R_a$)—; wherein said chain may optionally be substituted on carbon with 1, 2, or 3, oxo (═O), hydroxy, carboxy, halo, mercapto, nitro, —N($R_b$)($R_c$), ($C_3$–$C_6$)cycloalkyl, aryl, heteroaryl, saccharides, amino acids, or peptides; and wherein said chain may optionally be saturated or unsaturated;
- $R_2$ is carboxy, ($C_1$–$C_6$)alkanoyl, ($C_1$–$C_6$)alkoxycarbonyl, halo($C_1$–$C_6$)alkyl, —C(═O)N$R_d R_e$, a saccharide, an amino acid, a peptide, or ($C_1$–$C_6$)alkyl substituted by 1 or 2 hydroxy, ($C_1$–$C_6$)alkoxy, ($C_1$–$C_6$)alkanoyloxy, carboxy, amino acids, peptides, saccharides, or —C(═O)N$R_d R_e$;
- $R_3$ is hydrogen, ($C_1$–$C_6$)alkyl, ($C_1$–$C_6$)alkoxy, ($C_1$–$C_6$)alkylthio, aryl, heteroaryl, aryloxy, or heteroaryloxy;
- $R_4$ is hydrogen or ($C_1$–$C_6$)alkyl; and $R_5$ is hydroxy, ($C_1$–$C_6$)alkoxy, or ($C_1$–$C_6$)alkanoyloxy; or $R_4$ and $R_5$ taken together are ethylenedioxy;
- $R_6$ is hydrogen, carboxy, ($C_1$–$C_6$)alkanoyl, ($C_1$–$C_6$)alkoxycarbonyl, halo($C_1$–$C_6$)alkyl, —C(═O)N$R_f R_g$, a saccharide, an amino acid, a peptide, or ($C_1$–$C_6$)alkyl optionally substituted by 1 or 2 hydroxy, ($C_1$–$C_6$)alkoxy, ($C_1$–$C_6$)alkanoyloxy, carboxy, amino acids, peptides, saccharides, or —C(═O)N$R_f R_g$;
- $R_a$ is hydrogen, ($C_1$–$C_6$)alkyl, ($C_1$–$C_6$)alkanoyl, phenyl or benzyl; and
- $R_b$, $R_c$, $R_d$, $R_e$, $R_f$ and $R_g$ are each independently hydrogen, ($C_1$–$C_6$)alkyl, ($C_1$–$C_6$)alkanoyl, phenyl or benzyl; or $R_b$ and $R_c$, $R_d$ and $R_e$ or $R_f$ and $R_g$, together with the nitrogen to which they are attached, are pyrrolidino, piperidino, or morpholino;
- wherein any aryl, heteroaryl, aryloxy, or heteroaryloxy of Y, or $R_3$ may optionally be substituted by 1, 2, or 3 ($C_1$–$C_6$)alkyl, ($C_1$–$C_6$)alkoxy, ($C_1$–$C_6$)alkanoyl, ($C_1$–$C_6$)alkanoyloxy, ($C_1$–$C_6$)alkoxycarbonyl, hydroxy ($C_1$–$C_6$)alkyl, halo($C_1$–$C_6$)alkyl, hydroxy, halo, carboxy, mercapto, nitro, or —N($R_h$)($R_j$); wherein each $R_h$ and $R_j$ is independently hydrogen, ($C_1$–$C_6$)alkyl, ($C_1$–$C_6$)alkanoyl, phenyl or benzyl; or $R_h$ and $R_j$ together with the nitrogen to which they are attached are pyrrolidino, piperidino, or morpholino;

or a pharmaceutically acceptable salt thereof.

The invention also provides a compound of formula I wherein:

$R_1$ is —$(CH_2)_n$—(X)—(Y); n is 0 to 4; X is oxy, thio, —N($R_a$)—, or absent; Y is a monoprotected amino acid, a diprotected amino acid, a peptide, or a 1 to 15 membered branched or unbranched carbon chain optionally comprising 1, 2, or 3 non-peroxide oxy, thio, or —N($R_a$)—; wherein said chain is substituted with 1, 2, or 3 peptides; and wherein said chain may optionally be saturated or unsaturated;

$R_2$ is hydrogen or $(C_1-C_6)$alkyl; $R_3$ is hydrogen, $(C_1-C_6)$alkyl, $(C_1-C_6)$alkoxy, $(C_1-C_6)$alkylthio, aryl, heteroaryl, aryloxy, or heteroaryloxy; $R_4$ is hydrogen or $(C_1-C_6)$alkyl; and $R_5$ is hydroxy, $(C_1-C_6)$alkoxy, or $(C_1-C_6)$alkanoyloxy; or $R_4$ and $R_5$ taken together are ethylenedioxy; $R_6$ is hydrogen, carboxy, $(C_1-C_6)$alkanoyl, $(C_1-C_6)$alkoxycarbonyl, halo$(C_1-C_6)$alkyl, —C(=O)N$R_f R_g$, a saccharide, an amino acid, a peptide, or $(C_1-C_6)$alkyl optionally substituted by 1 or 2 hydroxy, $(C_1-C_6)$alkoxy, $(C_1-C_6)$alkanoyloxy, carboxy, amino acids, peptides, saccharides, or —C(=O)N$R_f R_g$; $R_a$ is hydrogen, $(C_1-C_6)$alkyl, $(C_1-C_6)$alkanoyl, phenyl or benzyl;

and $R_b$, $R_c$, $R_d$, $R_e$, $R_f$ and $R_g$ are each independently hydrogen, $(C_1-C_6)$alkyl, $(C_1-C_6)$alkanoyl, phenyl or benzyl; or $R_b$ and $R_c$, $R_d$ and $R_e$, or $R_f$ and $R_g$, together with the nitrogen to which they are attached, are pyrrolidino, piperidino, or morpholino; wherein any aryl, heteroaryl, aryloxy, or heteroaryloxy of Y, or $R_3$ may optionally be substituted by 1, 2, or 3 $(C_1-C_6)$allyl, $(C_1-C_6)$alkoxy, $(C_1-C_6)$alkanoyl, $(C_1-C_6)$alkanoyloxy, $(C_1-C_6)$alkoxycarbonyl, hydroxy$(C_1-C_6)$alkyl, halo$(C_1-C_6)$alkyl, hydroxy, halo, carboxy, mercapto, nitro, or —N($R_h$)($R_j$); wherein each $R_h$ and $R_j$ is independently hydrogen, $(C_1-C_6)$alkyl, $(C_1-C_6)$alkanoyl, phenyl or benzyl; or $R_h$ and $R_j$ together with the nitrogen to which they are attached are pyrrolidino, piperidino, or morpholino; or a pharmaceutically acceptable salt thereof. Preferably, Y is $(C_1-C_6)$alkyl substituted with a peptide.

The invention also provides a compound of formula I wherein:

$R_1$ is hydrogen, hydroxy, mercapto, amino, halo, carboxy, nitro, or —$(CH_2)_n$—(X)—(Y); n is 0 to 4; X is oxy, thio, —N($R_a$)—, or absent; Y is $(C_3-C_6)$cycloalkyl, aryl, heteroaryl, a saccharide, an amino acid, a peptide, or a 1 to 15 membered branched or unbranched carbon chain optionally comprising 1, 2, or 3 non-peroxide oxy, thio, or —N($R_a$)—; wherein said chain may optionally be substituted on carbon with 1, 2, or 3, oxo, hydroxy, carboxy, halo, mercapto, nitro, —N($R_b$)($R_c$), $(C_3-C_6)$cycloalkyl, aryl, heteroaryl, saccharides, amino acids, or peptides; and wherein said chain may optionally be saturated or unsaturated;

$R_2$ is hydrogen or $(C_1-C_6)$alkyl; $R_3$ is hydrogen, $(C_1-C_6)$alkyl, $(C_1-C_6)$alkoxy, $(C_1-C_6)$alkylthio, aryl, heteroaryl, aryloxy, or heteroaryloxy; $R_4$ is hydrogen or $(C_1-C_6)$alkyl; and $R_5$ is hydroxy, $(C_1-C_6)$alkoxy, or $(C_1-C_6)$alkanoyloxy; or $R_4$ and $R_5$ taken together are ethylenedioxy; $R_6$ is carboxy, $(C_1-C_6)$alkanoyl, $(C_1-C_6)$alkoxycarbonyl, —C(=O)N$R_f R_g$, a saccharide, an amino acid, a peptide, or $(C_1-C_6)$alkyl substituted by 1 or 2 $(C_1-C_6)$alkoxy, $(C_1-C_6)$alkanoyloxy, carboxy, amino acids, peptides, saccharides, or —C(=O)N$R_f R_g$; $R_a$ is hydrogen, $(C_1-C_6)$alkyl, $(C_1-C_6)$alkanoyl, phenyl or benzyl; and $R_b$, $R_c$, $R_d$, $R_e$, $R_f$ and $R_g$ are each independently hydrogen, $(C_1-C_6)$alkyl, $(C_1-C_6)$alkanoyl, phenyl or benzyl;

or $R_b$ and $R_c$, $R_d$ and $R_e$, or $R_f$ and $R_g$, together with the nitrogen to which they are attached, are pyrrolidino, piperidino, or morpholino; wherein any aryl, heteroaryl, aryloxy, or heteroaryloxy of Y, or $R_3$ may optionally be substituted by 1, 2, or 3 $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, hydroxy$(C_1-C_6)$alkyl, halo$(C_1-C_6)$alkyl, hydroxy, halo, carboxy, mercapto, nitro, or —N($R_h$)($R_j$); wherein each $R_h$ and $R_j$ is independently hydrogen, $(C_1-C_6)$alkyl, $(C_1-C_6)$alkanoyl, phenyl or benzyl; or $R_h$ and $R_j$ together with the nitrogen to which they are attached are pyrrolidino, piperidino, or morpholino; or a pharmaceutically acceptable salt thereof.

The invention also provides dimeric compounds comprising two compounds of formula (I), connected by a linker. The linker can be, for example, an alkyl or ester based linker group. Examples of suitable linkers include —$(CH_2)_p$—O—$(CH_2)_q$—, —$(CH_2)_r$—, and —$CH_2$—S—$CH_2C(O)$—O—$(CH_2)_2$—O—$C(O)CH_2$—S—$CH_2$—; wherein p and q are each individually an integer from 1 to 8, inclusive; and r is an integer from 1 to 16, inclusive. Preferably, r is an integer from 1 to 8, inclusive. As would be apparent to one skilled in the art, other linkers of approximately the same length can also be used. Two compounds of formula I can conveniently be linked, for example, by replacing $R_1$, $R_3$, $R_4$ or $R_5$, independently, on each compound of formula I, with the bifunctional linker. When the linkage is through $R_1$, the linker is preferably —$CH_2$—O—$CH_2$— or —$CH_2$—S—$CH_2C(O)$—O—$(CH_2)_2$—O—$C(O)CH_2$—S—$CH_2$—.

The invention also provides compounds of formula I wherein $R_1$ is —$(CH_2)_n$—(X)—(Y); n is 1 to 4 (preferably n is 1); X is oxy, thio, or —N($R_a$)—(preferably X is thio); Y is a 2 to 15 membered branched or unbranched carbon chain optionally comprising 1, 2, or 3 non-peroxide oxy, thio, or —N($R_a$)—; wherein said chain is substituted on carbon with 1, 2, or 3, oxo, carboxy, mercapto, —N($R_b$)($R_c$), $(C_3-C_6)$cycloalkyl, aryl, heteroaryl, saccharides, amino acids, or peptides; and wherein said chain may optionally be saturated or unsaturated (preferably Y is a 2 to 6 membered branched or unbranched carbon chain that is substituted on carbon with 1, 2, or 3, oxo, heteroaryl, amino acids, or peptides); $R_2$ is hydrogen or $(C_1-C_6)$alkyl; $R_3$ is hydrogen, $(C_1-C_6)$alkyl, $(C_1-C_6)$alkoxy, $(C_1-C_6)$alkylthio, aryl, heteroaryl, aryloxy, or heteroaryloxy; $R_4$ is hydrogen or $(C_1-C_6)$alkyl; and $R_5$ is hydroxy, $(C_1-C_6)$alkoxy, or $(C_1-C_6)$alkanoyloxy; or $R_4$ and $R_5$ taken together are ethylenedioxy; $R_6$ is hydrogen, carboxy, $(C_1-C_6)$alkanoyl, $(C_1-C_6)$alkoxycarbonyl, halo$(C_1-C_6)$alkyl, —C(=O)N$R_f R_g$, a saccharide, an amino acid, a peptide, or $(C_1-C_6)$alkyl optionally substituted by 1 or 2 hydroxy, $(C_1-C_6)$alkoxy, $(C_1-C_6)$alkanoyloxy, carboxy, amino acids, peptides, saccharides, or —C(=O)N$R_f R_g$; $R_a$ is hydrogen, $(C_1-C_6)$alkyl, $(C_1-C_6)$alkanoyl, phenyl or benzyl; and $R_b$, $R_c$, $R_f$ and $R_g$ are each independently hydrogen, $(C_1-C_6)$alkyl, $(C_1-C_6)$alkanoyl, phenyl or benzyl; or $R_b$ and $R_c$, or $R_f$ and $R_g$, together with the nitrogen to which they are attached, are pyrrolidino, piperidino, or morpholino; wherein any aryl, heteroaryl, aryloxy, or heteroaryloxy of Y, or $R_3$ may optionally be substituted by 1, 2, or 3 $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, hydroxy$(C_1-C_6)$alkyl, halo$(C_1-C_6)$alkyl, hydroxy, halo, carboxy, mercapto, nitro, or —N($R_h$)($R_j$); wherein each $R_h$ and $R_j$ is independently hydrogen, $(C_1-C_6)$alkyl, $(C_1-C_6)$alkanoyl, phenyl or benzyl; or $R_h$ and $R_j$ together with the nitrogen to which they are attached are pyrrolidino, piperidino, or morpholino; or a pharmaceutically acceptable salt thereof.

The invention also provides a compound of formula II:

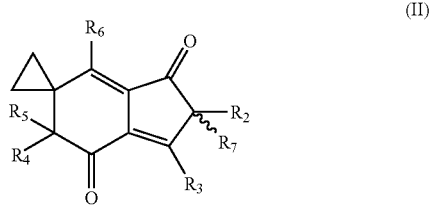

(II)

wherein
$R_2$ is $(C_1-C_6)$alkyl;
$R_3$ is hydrogen, $(C_1-C_6)$alkyl, $(C_1-C_6)$alkoxy, $(C_1-C_6)$alkylthio, aryl, heteroaryl, aryloxy, or heteroaryloxy;
$R_4$ is hydrogen or $(C_1-C_6)$alkyl; and $R$ is hydroxy, $(C_1-C_6)$alkoxy, or $(C_1-C_6)$alkanoyloxy; or $R_4$ and $R_5$ taken together are ethylenedioxy;
$R_6$ is hydrogen, carboxy, $(C_1-C_6)$alkanoyl, $(C_1-C_6)$alkoxycarbonyl, halo$(C_1-C_6)$alkyl, —C(=O)NR$_f$R$_g$, a saccharide, an amino acid, a peptide, or $(C_1-C_6)$alkyl optionally substituted by 1 or 2 hydroxy, $(C_1-C_6)$alkoxy, $(C_1-C_6)$alkanoyloxy, carboxy, amino acids, peptides, saccharides, or —C(=O)NR$_f$R$_g$;
$R_7$ is carboxy, $(C_1-C_6)$alkanoyl, $(C_1-C_6)$alkoxycarbonyl, halo$(C_1-C_6)$alkyl, —C(=O)NR$_d$R$_e$, a saccharide, an amino acid, a peptide, or $(C_1-C_6)$alkyl substituted by 1 or 2 hydroxy, $(C_1-C_6)$alkoxy, $(C_1-C_6)$alkanoyloxy, carboxy, amino acids, peptides, saccharides, or —C(=O)NR$_d$R$_e$;
$R_d$, $R_e$, $R_f$ and $R_g$ are each independently hydrogen, $(C_1-C_6)$alkyl, $(C_1-C_6)$alkanoyl, phenyl or benzyl; or $R_d$ and $R_e$, or $R_f$ and $R_g$, together with the nitrogen to which they are attached, are pyrrolidino, piperidino, or morpholino;
wherein any aryl, heteroaryl, aryloxy, or heteroaryloxy of $R_3$ may optionally be substituted by 1, 2, or 3 $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, hydroxy$(C_1-C_6)$alkyl, halo$(C_1-C_6)$alkyl, hydroxy, halo, carboxy, mercapto, nitro, or —N(R$_h$)(R$_j$); wherein each R$_h$ and R$_j$ is independently hydrogen, $(C_1-C_6)$alkyl, $(C_1-C_6)$alkanoyl, phenyl or benzyl; or R$_h$ and R$_j$ together with the nitrogen to which they are attached are pyrrolidino, piperidino, or morpholino;
or a pharmaceutically acceptable salt thereof.

Compounds of the invention are useful as antineoplastic agents, i.e., to inhibit tumor cell growth in vitro or in vivo, in mammalian hosts, such as humans or domestic animals, and are particularly effective against solid tumors and multidrug resistant tumors. Thus, the invention provides a method comprising inhibiting cancer cells, by contacting said cells, in vitro or in vivo, with an effective amount of a compound of the invention. The invention also provides a therapeutic method comprising treating cancer (i.e., inhibiting tumor cell growth) by administering a compound of the invention to a mammal (e.g. a human) in need of such therapy.

The present compounds may be targeted to a particular tumor by attaching the compound to a reagent which is capable of binding to a tumor-associated antigen. The antigen may be located on a tumor or in the tumor cell area. Suitable reagents include polyclonal and monoclonal antibodies. The compound-reagent complex or conjugate may further comprise a linker (e.g. a linker as described hereinabove) for attaching the compound to the reagent. Accordingly, the invention also provides a compound comprising a compound of formula I or formula II and a reagent (e.g. a polyclonal or monoclonal antibody) which is capable of binding to a tumor-associated antigen.

The present invention also provides a pharmaceutical composition (e.g. a pharmaceutical unit dosage form), comprising one or more compounds of the invention in combination with a pharmaceutically acceptable diluent or carrier.

The invention also provides a compound of the invention (e.g. a compound of formula I or II, a dimer thereof, or a conjugate comprising a compound of formula I or II and a reagent that is capable of binding to a tumor-associated antigen, or a salt thereof) for use in medical therapy (preferably for use in treating cancer, e.g. solid tumors), as well as the use of a compound of the invention for the manufacture of a medicament useful for the treatment of cancer, e.g. solid tumors.

The invention also provides processes and novel intermediates disclosed herein that are useful for preparing compounds of the invention. Some of the compounds of the invention are useful to prepare other compounds of the invention.

DETAILED DESCRIPTION

Figure 1A:
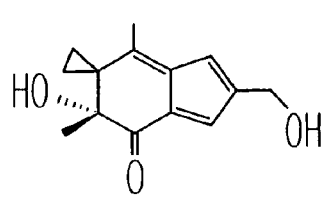
FIG. 1 shows representative compounds of the invention (compounds 1 to 9) and intermediate compounds 10 or 11.
Figure 1B:
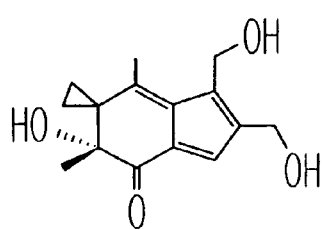
Figure 1C:
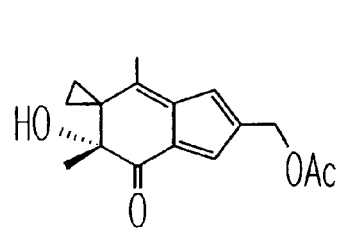
Figure 1D:
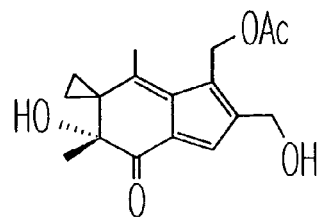
Figure 1E:
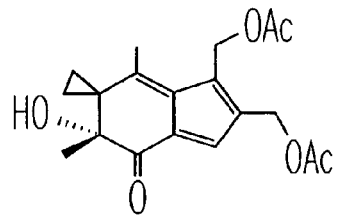
Figure 1F:
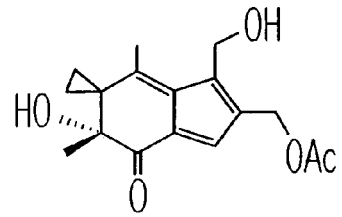
Figure 1G:
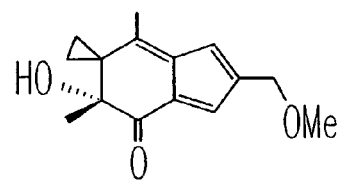
Figure 1H:
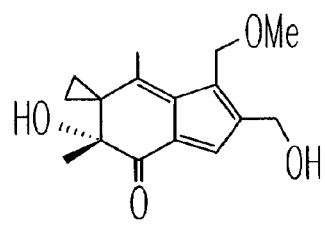
Figure 1I:
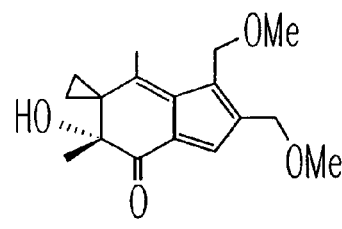
Figure 1J:
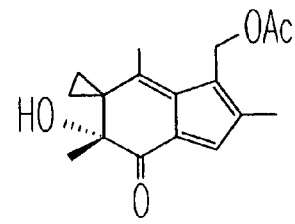
Figure 1K:
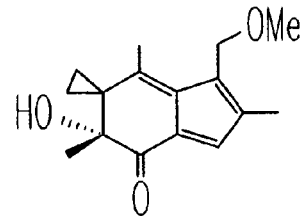
Figure 2A:
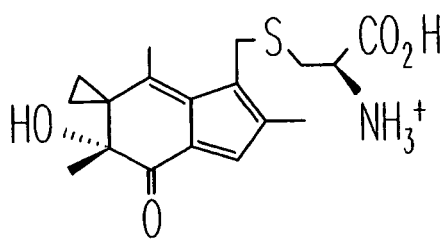
FIG. 2 shows representative compounds of the invention (compounds 13 to 16).
Figure 2B:
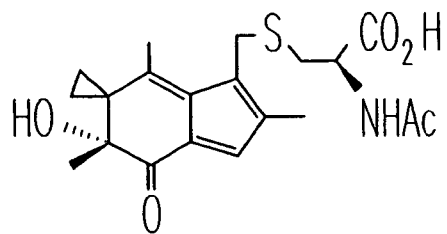
Figure 2C:
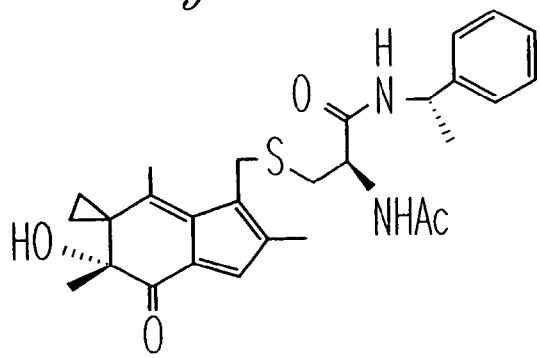
Figure 2D:
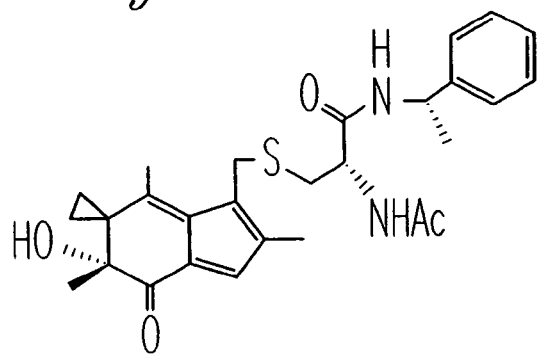
Figure 2E:
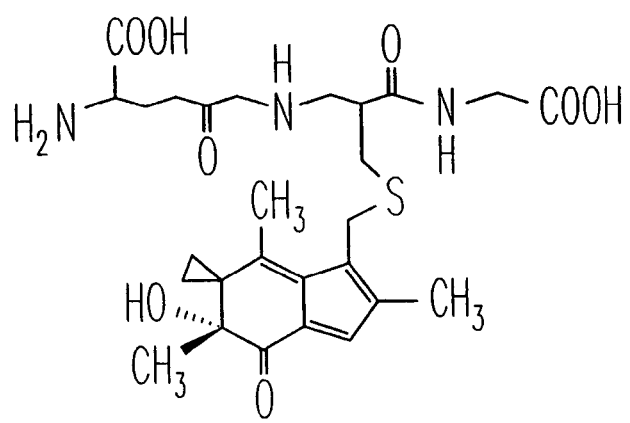
Figures 3A, 3B:
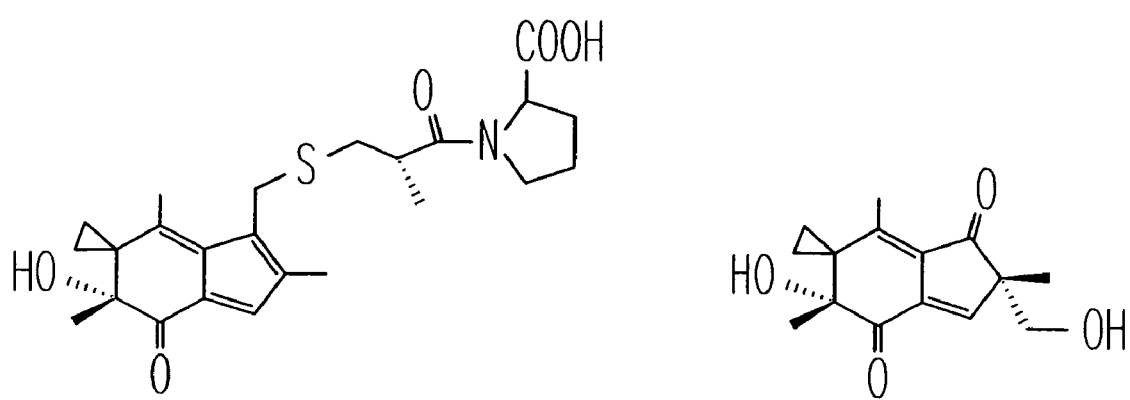
FIG. 3 shows representative compounds of the invention (compounds 17 and 18).

The following definitions are used, unless otherwise described: halo is fluoro, chloro, bromo, or iodo. Alkyl, alkoxy, alkenyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four non-peroxide oxygen, sulfur, or N(R$_y$) wherein R$_y$ is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "inhibit" or "inhibiting" means decreasing tumor cell growth rate from the rate which would occur without treatment, and/or causing tumor mass to decrease. Inhibiting also includes causing a complete regression of the tumor. Thus, the present analogs can either be cytostatic or cytotoxic to tumor cells.

The method of the invention can be practiced on any mammal having a susceptible cancer, i.e., a malignant cell population or tumor. Compounds of the invention are effective on human tumors in vivo as well as on human tumor cell lines in vitro. The present compounds may be particularly useful for the treatment of solid tumors for which relatively few treatments are available. Such tumors include epidermoid and myeloid tumors, acute (AML) or chronic (CML). Such tumors also include, nonsmall cell, squamous, liver, cervical, renal, adrenal, stomach, esophageal, oral and mucosal tumors, as well as lung, ovarian, breast and colon carcinoma, and melanomas (including amelanotic subtypes). The present compounds can also be used against endometrial tumors, bladder cancer, pancreatic cancer, lymphoma, Hodgkin's disease, prostate cancer, sarcomas and testicular cancer as well as against tumors of the central nervous system, such as brain tumors, neuroblastomas and hematopoietic cell cancers such as B-cell leukemia/lymphomas, myelomas, T-cell leukemia/lymphomas, small cell leukemia/lymphomas, as well as null cell, sezary, monocytic, myelomonocytic and Hairy cell leukemia. These leukemia/lymphomas can be either acute (ALL) or chronic (CLL).

The term "saccharide" includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995. A saccharide can conveniently be linked to the remainder of a compound of formula I or II through an ether bond.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

It has been shown that certain peptides specifically bind to specific tumor-associated antigens in a manner analogous to the binding of antibodies to such antigens. See Arap et al. *Science*, 1998, 279, 5349, 377–380. Thus, pharmaceutical agents which comprise a peptide that is capable of binding to specific receptors on tumor cells, can be delivered preferentially to such tumor cells. As a result, one preferred embodiment of the invention provides a compound of formula I or II comprising a peptide capable of specifically binding to a tumor-associated antigen. Preferred peptides include -Cys-Asp-Cys-Arg-Gly-Asp-Cys-Phe-Cys (SEQ ID NO:1), -Cys-Asp-Gly-Arg-Cys (SEQ ID NO:2), and -Cys-Asp-Gly-Cys-Lys-Asn-Phe-Phe-Trp-Lys-Thr-Phe-Thr-Ser-Cys (SEQ ID NO:3).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-tumor activity using Test A or Test B, described hereinbelow, or using other tests which are well known in the art. In preferred compounds of formula I, the absolute stereochemistry at the carbon bearing $R_4$ and $R_5$ is (R).

Specific values listed below for radicals, substituents, and ranges, are for illustration only; they do not exclude other defined values or other values within defined ranges for the radicals and substituents.

Specifically, $(C_1-C_4)$alkyl can be methyl, ethyl, propyl, isopropyl, butyl, iso-butyl, or sec-butyl; $(C_1-C_6)$alkyl can be methyl, ethyl, propyl, isopropyl, butyl, iso-butyl, sec-butyl, pentyl, 3-pentyl, or hexyl; $(C_1-C_8)$alkyl can be methyl, ethyl, propyl, isopropyl, butyl, iso-butyl, sec-butyl, pentyl, 3-pentyl, hexyl, septyl, or octyl; $(C_3-C_6)$cycloalkyl can be cyclopropyl, cyclobutyl, cyclopentyl, or cyclohexyl; $(C_1-C_4)$alkoxy can be methoxy, ethoxy, propoxy, isopropoxy, butoxy, iso-butoxy, or sec-butoxy; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 2-methyl-2-propenyl, 1-pentenyl, 2-pentenyl, 3-pentenyl, 4-pentenyl, 3-methyl-2-butenyl, 3-methyl-3-butenyl, 1-hexenyl, 2-hexenyl, 3-hexenyl, 4-hexenyl, 5-hexenyl, or 4-methyl-3-pentenyl; $(C_1-C_6)$alkanoyl can be acetyl, propanoyl or butanoyl; halo$(C_1-C_6)$alkyl can be iodomethyl, bromomethyl, chloromethyl, fluoromethyl, trichloromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$, is hydroxy, halo, carboxy, aryl, heteroaryl, a saccharide, an amino acid, or a peptide.

Another specific value for $R_1$ is —$(CH_2)_n$—(X)—(Y); wherein n is 0 to 4; X is oxy, thio, —N($R_a$)—, or absent; and Y is a peptide, or ($C_1$–$C_6$)alkyl substituted with a peptide.

Another specific value for $R_1$ is hydrogen or ($C_1$–$C_6$) alkyl, optionally substituted with 1 or 2 hydroxy, halo, methoxy or ethoxy.

Another specific value for $R_1$ is —$(CH_2)_n$—(X)—(Y); X is oxy, thio, or —N($R_a$)—; and Y is $CH_2OC(O)(C_1$–$C_4)$ alkyl, $CH_2C(O)$—O—$(CH_2)_2$—O—$C(O)CH_2SH$, $(CH_2)_2$—O—$(CH_2)_2$halo, ($C_1$–$C_4$)alkyl—O—($C_1$–$C_4$)alkyl, $CH_2CO_2(C_1$–$C_4)$alkyl $CH_2CO_2H$, aryl($C_1$–$C_4$)alkyl, a saccharide, an amino acid, or ($C_1$–$C_8$)alkyl optionally substituted with 1 or 2 hydroxy or halo; wherein any aryl or heteroaryl of Y may optionally be substituted with 1 or 2 hydroxy, halo, ($C_1$–$C_4$)alkyl or ($C_1$–$C_4$)alkoxy.

Another specific value for $R_1$ is —$CH_2$—(X)—(Y), wherein X is oxy, thio, or —N($R_a$)—; and Y is ($C_1$–$C_8$)alkyl optionally substituted with 1 or 2 hydroxy, halo, carboxy, oxo, mercapto, —N($R_b$)($R_c$), ($C_3$–$C_6$)cycloalkyl, aryl, heteroaryl, saccharides, amino acids, or peptides; wherein any aryl or heteroaryl of Y may optionally be substituted by 1, 2, or 3($C_1$–$C_6$)alkyl, ($C_1$–$C_6$)alkoxy, ($C_1$–$C_6$)alkanoyl, ($C_1$–$C_6$)alkanoyloxy, ($C_1$–$C_6$)alkoxycarbonyl, hydroxy($C_1$–$C_6$)alkyl, halo($C_1$–$C_6$)alkyl, hydroxy, halo, carboxy, mercapto, nitro, or —N($R_h$)($R_j$); wherein each $R_h$ and $R_j$ is independently hydrogen, ($C_1$–$C_6$)alkyl, ($C_1$–$C_6$)alkanoyl, phenyl or benzyl; or $R_h$ and $R_j$ together with the nitrogen to which they are attached form a pyrrolidino, piperidino, or morpholino radical.

Another specific value for $R_1$ is —$(CH_2)_n$—(X)—(Y); n is 1 or 2; X is oxy, thio, or —N($R_a$)—; and Y is ($C_1$–$C_6$)alkyl or ($C_2$–$C_6$)alkenyl, optionally substituted with 1 or 2 oxo, hydroxy, carboxy, halo, mercapto, nitro, —N($R_b$)($R_c$), ($C_3$–$C_6$)cycloalkyl, aryl, heteroaryl, saccharides, amino acids, or peptides; wherein any aryl or heteroaryl of Y may optionally be substituted by 1, 2, or 3 ($C_1$–$C_6$)alkyl, ($C_1$–$C_6$) alkoxy, ($C_1$–$C_6$)alkanoyl, ($C_1$–$C_6$)alkanoyloxy, ($C_1$–$C_6$) alkoxycarbonyl, hydroxy($C_1$–$C_6$)alkyl, halo($C_1$–$C_6$)alkyl, hydroxy, halo, carboxy, mercapto, nitro, and —N($R_h$)($R_j$); wherein each $R_h$ and $R_j$ is independently hydrogen, ($C_1$–$C_6$) alkyl, ($C_1$–$C_6$)alkanoyl, phenyl and benzyl; or $R_h$ and $R_j$ together with the nitrogen to which they are attached form a pyrrolidino, piperidino, or morpholino radical.

Another specific value for $R_1$ is —$CH_2$-[sulfur-linked-cysteine]-$R_x$ wherein $R_x$ is an amino acid or a peptide comprising 2 to 24 amino acids.

Another specific value for $R_1$ is —$CH_2$-[sulfur-linked —N-acylcysteine]-R wherein $R_x$ is an amino acid or a peptide comprising 2 to 24 amino acids.

Another specific value for $R_1$ is —$CH_2$-[sulfur-linked-glutathione].

Another specific value for $R_1$ is 2-[(R)-α-methylbenzylaminocarbonyl]-2-(acylamino)ethylthiomethyl. Preferably, the 2-position of the ethyl group has the (S) configuration of cysteine.

A more specific value for $R_1$ is hydrogen, methyl, hydroxymethyl, methoxymethyl, or acetoxymethyl.

A specific value for $R_2$ is hydroxymethyl, methoxymethyl, or acetoxymethyl.

Another specific value for $R_2$ is carboxy, ($C_1$–$C_6$)alkanoyl, ($C_1$–$C_6$)alkoxycarbonyl, or —C(=O)$NR_dR_e$.

Another specific value for $R_2$ is ($C_1$–$C_6$)alkyl substituted by 1 or 2 hydroxy, ($C_1$–$C_6$)alkoxy, ($C_1$–$C_6$)alkanoyloxy, carboxy, amino acids, peptides, saccharides, or —C(=O)$NR_dR_e$.

Another specific value for $R_2$ is —$CH_2$-[sulfur-linked-cysteine]-$R_x$ wherein $R_x$ is an amino acid or a peptide comprising 2 to 24 amino acids.

Another specific value for $R_2$ is —$CH_2$-[sulfur-linked —N-acylcysteine]-R wherein $R_x$ is an amino acid or a peptide comprising 2 to 24 amino acids.

Another specific value for $R_2$ is —$CH_2$-[sulfur-linked-glutathione].

A specific value for $R_3$ is hydrogen.
A specific value for $R_4$ is methyl.
A specific value for $R_5$ is hydroxy.
A specific value for $R_6$ is hydrogen.
A specific value for $R_6$ is carboxy, ($C_1$–$C_6$)alkanoyl, ($C_1$–$C_6$)alkoxycarbonyl, or —C(=O)$NR_fR_g$.

A specific value for $R_6$ is ($C_1$–$C_6$)alkyl optionally substituted by 1 or 2 hydroxy, ($C_1$–$C_6$)alkoxy, ($C_1$–$C_6$)alkanoyloxy, carboxy, amino acids, peptides, saccharides, or —C(=O)$NR_fR_g$.

Another specific value for $R_6$ is —$CH_2$-[sulfur-linked-cysteine]-$R_x$ wherein $R_x$ is an amino acid or a peptide comprising 2 to 24 amino acids.

Another specific value for $R_6$ is —$CH_2$-[sulfur-linked —N-acylcysteine]-R wherein $R_x$ is an amino acid or a peptide comprising 2 to 24 amino acids.

A more specific value for $R_6$ is methyl or hydroxymethyl.

A specific value for $R_7$ is ($C_1$–$C_6$)alkyl substituted by 1 or 2 hydroxy, ($C_1$–$C_6$)alkoxy, ($C_1$–$C_6$)alkanoyloxy, carboxy, amino acids, peptides, saccharides, or —C(=O)$NR_dR_e$.

A specific value for $R_7$ is hydroxymethyl.

Specifically, $R_x$ can be a peptide comprising 4 to 20 amino acids.

Another specific value for $R_x$ is -Leu-Gly-Phe, -Phe-Leu-Gly, -Leu-Leu-Phe, -Gly-Phe, or -Leu.

Another specific value for $R_x$ is -Asp-Cys-Arg-Gly-Asp-Cys-Phe-Cys (SEQ ID NO:4), -Asp-Gly-Arg-Cys (SEQ ID NO:5), or -Asp-Gly-Cys-Lys-Asn-Phe-Phe-Trp-Lys-Thr-Phe-Thr-Ser-Cys (SEQ ID NO:5).

A specific compound of the invention is a compound of formula I wherein $R_2$ is ($C_1$–$C_6$)alkyl, substituted with hydroxy, ($C_1$–$C_6$)alkoxy, ($C_1$–$C_6$)alkanoyloxy, or carboxy; $R_3$ is H, ($C_1$–$C_6$)alkyl, ($C_1$–$C_6$)alkoxy, ($C_1$–$C_6$)alkylthio, aryl, heteroaryl, aryloxy, or heteroaryloxy; $R_4$ is hydrogen or ($C_1$–$C_6$)alkyl; $R_5$ is hydroxy; and $R_6$ is ($C_1$–$C_6$)alkyl, optionally substituted with hydroxy, ($C_1$–$C_6$)alkoxy, ($C_1$–$C_6$)alkanoyloxy, or carboxy; or a pharmaceutically acceptable salt thereof.

Another specific compound of the invention is a compound of formula I wherein $R_1$ is hydrogen or ($C_1$–$C_6$)alkyl, optionally substituted with hydroxy, halo, methoxy, ethoxy, or acetoxy; $R_2$ is hydroxymethyl, methoxymethyl, or acetoxymethyl; $R_3$ is hydrogen; $R_4$ is methyl; $R_5$ is hydroxy; and $R_6$ is methyl or hydroxymethyl; or a pharmaceutically acceptable salt thereof.

Another specific compound of the invention is a compound of formula I wherein $R_1$ is —$(CH_2)_n$—(X)—(Y); n is 0 to 4; X is oxy, thio, —N($R_a$)—, or absent; Y is a monoprotected amino acid or a diprotected amino acid; and $R_2$ is hydrogen or ($C_1$–$C_6$)alkyl; or a pharmaceutically acceptable salt thereof.

Another specific compound of the invention is a compound of formula I wherein $R_1$ is —$CH_2$-[sulfur-linked —N-acylcysteine], (S)-2-[(R)-α-methylbenzylaminocarbonyl]-2-(acylamino)ethylthiomethyl, or (R)-2-[(R)-α-methylbenzylaminocarbonyl]-2-(acylamino)ethylthiomethyl; and $R_2$ is hydrogen or $(C_1-C_6)$alkyl; or a pharmaceutically acceptable salt thereof.

A specific compound of formula I is a compound which is:

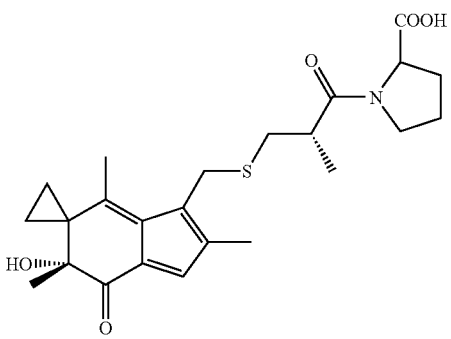

or a pharmaceutically acceptable salt thereof.

A specific compound of formula II is a compound which is

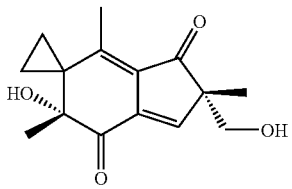

or a pharmaceutically acceptable salt thereof.

A preferred compound is a compound of formula I wherein $R_4$ is hydrogen or $(C_1-C_6)$alkyl; and RP is hydroxy or acetoxy; wherein the absolute stereochemistry at the carbon bearing $R_4$ and $R_5$ is (R); or a pharmaceutically acceptable salt thereof.

Processes for preparing compounds of the invention are provided as further embodiments of the invention and are illustrated by the following procedures in which the meanings of the generic radicals are as given above unless otherwise qualified.

The compounds of the present invention (compounds of formula I and II and salts thereof) may be derived from illudin S, hydroxymethyl acylfulvene (HMAF, i.e., a compound of formula (I) wherein $R_1$ is $CH_2OH$, $R_2$ is $CH_3$, $R_3$ is hydrogen, $R_4$ is $CH_3$, $R_5$ is OH and $R_6$ is $CH_3$) and fulvene (i.e., a compound of formula (I) wherein $R_1$ is H, $R_2$ is $CH_3$, $R_3$ is H, $R_4$ is $CH_3$, $R_5$ is OH and $R_6$ is $CH_3$) the syntheses of which are known in the art (see e.g., WO 91/04754; WO 94/18151).

A compound of formula I wherein $R_2$ is hydroxymethyl can be prepared by oxidation of a corresponding compound of formula I wherein $R_2$ is methyl. The oxidation can conveniently be carried out using selenium dioxide and tert-butyl hydroperoxide under conditions similar to those described in Example 1.

A compound of formula I wherein $R_1$ is hydroxymethyl can be prepared from a corresponding compound of formula I wherein $R_1$ is hydrogen by treatment with paraformaldehyde and sulfuric acid. The reaction can conveniently be carried out under conditions similar to those described in Example 2.

A compound of formula I wherein $R_2$ is acetoxymethyl can be prepared by acylation of a corresponding compound of formula I wherein $R_2$ is hydroxymethyl. The acylation can conveniently be carried out using acetic anhydride, under conditions similar to those described in Example 3.

A compound of formula I wherein $R_2$ is methoxymethyl can be prepared by reacting a corresponding compound of formula I wherein $R_2$ is hydroxymethyl with methyl iodide and silver oxide. The reaction can conveniently be carried out under conditions similar to those described in Example 7.

A compound of formula I wherein $R_1$ is methoxymethyl can be prepared by reacting a corresponding compound of formula I wherein $R_1$ is hydroxymethyl with methanol and sulfuric acid. The reaction can conveniently be carried out under conditions similar to those described in Example 8, sub-part a.

A compound of formula I wherein $R_1$ is —$CH_2$-[sulfur-linked-cysteine] can be prepared by reacting a corresponding compound of formula I wherein $R_1$ is hydroxymethyl by coupling with cysteine. The reaction can conveniently be carried out under conditions similar to those described in Example 10.

A compound of formula I wherein $R_1$ is —$CH_2$-[sulfur-linked-N-acylcysteine] can be prepared by reacting a corresponding compound of formula I wherein $R_1$ is hydroxymethyl by coupling with N-acylcysteine. The reaction can conveniently be carried out under conditions similar to those described in Example 11.

A compound of formula I wherein $R_1$ is 2-[(R)-α-methylbenzyl-aminocarbonyl]-2-(acylamino)ethylthiomethyl can be prepared by reacting a corresponding compound of formula I wherein $R_1$ is —$CH_2$-[sulfur-linked-N-acylcysteine] with α-methylbenzylamine. The reaction can conveniently be carried out under conditions similar to those described in Example 12.

A compound of formula I wherein $R_1$ is —$CH_2$-[sulfur-linked-glutathione] can be prepared by reacting a corresponding compound of formula I wherein $R_1$ is hydroxymethyl with glutathione. The reaction can conveniently be carried out under conditions similar to those described in Example 14.

A compound of formula I wherein $R_1$ is —$CH_2$-[sulfur-linked-cysteine]-$R_x$, or —$CH_2$-[sulfur-linked-N-acylcysteine]-$R_x$, can be prepared by reacting a corresponding compound of formula I wherein $R_1$ is —$CH_2$-[sulfur-linked-cysteine] or —$CH_2$-[sulfur-linked-N-acylcysteine] with the requisite amino acid or peptide ($R_x$). The reaction can conveniently be carried out under conditions similar to those described in Example 15.

Compounds of formula II can conveniently be prepared from illudin S using procedures similar to those described in Example 17.

Compounds of the invention can also be prepared using techniques and intermediates similar to those described by T. McMorris et al. *Tetrahedron*, 1997, 53, 44, 14579–14590; T. McMorris et al. *J. Org. Chem.* 1997, 62, 3015–3018; T. McMorris et al. *Chem. Comm.* 1997, 315–316; and T. McMorris et al. *Experentia* 1996, 52, 75–80; and those disclosed in U.S. Pat. Nos. 5,439,942; 5,439,936; 5,523,490; 5,536,176; WO 91/04754; WO 94/18151 and WO 98/03458. Some compounds of formula I or II can be used to prepare other compounds of formula I or II.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the invention can be formulated as pharmaceutical compositions and administered to a mammalian host, such as a human patient in a variety of dosage forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the invention can be determined by correlating their in vitro activity, and in vivo activity in animal models, such as murine or dog models as taught for illudin analogs such as those of U.S. Pat. Nos. 5,439,936 and 5,523,490, to activity in higher mammals, such as children and adult humans as taught, e.g., in Borch et al. (U.S. Pat. No. 4,938,949).

The therapeutically effective amount of analog necessarily varies with the subject and the tumor to be treated. It has been found that relatively high doses of representative compounds of the invention can be administered due to the decreased toxicity compared to illudin S and M. For example, the maximum tolerated dose of Illudin S is about 250 ug/kg, whereas compound 2 can be chronically administered at 35 mg/kg without toxicity. A therapeutic amount between 30 to 112,000 μg per kg of body weight is especially effective for intravenous administration while 300 to 112,000 μg per kg of body weight is effective if administered intraperitoneally. As one skilled in the art would recognize, the amount can be varied depending on the method of administration. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound can conveniently be administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day.

The cytotoxic and anti-tumor properties of a compound of the invention can be determined using pharmacological models which are well known to the art, or using Test A and Test B described below.

Test A. In Vitro Studies

To assess cytotoxic effects, various concentrations of compounds of the invention were added to cultures of MV522 (human lung carcinoma cell line), HL60 (myeloid leukemia cells), and 8392 (B-cell leukemia/lymphoma) cells for 48 hours, then cell growth/viability was determined by trypan blue exclusion. As an alternative to 48 hour continuous exposure studies, cells were plated in liquid culture in 96 well plates, exposed to various concentrations of compounds of the invention for 2 hours, pulsed with [$^3$H]-thymidine for one to two hours and harvested onto filter papers. The filter papers were added to vials containing scintillation fluid and residual radioactivity determined in a beta (scintillation) counter.

Data from Test A, for representative compounds of the invention, is shown in Table 1. Values are reported as mean±1 standard deviation; units are nanomoles per liter; and NT signifies not tested.

TABLE 1

| | 2 hour $IC_{50}$ (nm/l) | | |
|---|---|---|---|
| Compound | MV522 | HL60 | 8392 |
| 1 | 2,640 ± 360 | NT | 37,000 ± 2,300 |
| 2 | 11,300 ± 1,500 | NT | NT |
| 3 | 19,600 ± 9,700 | 15,600 ± 4,600 | 62,000 ± 3,600 |
| 4 | 20,400 ± 6300 | >40,000 | NT |
| 5 | 24,000 ± 6,100 | 38,400 ± 9,000 | NT |
| 6 | NT | NT | NT |
| 7 | 7,700 ± 3,500 | 6,000 ± 1,200 | NT |
| 8 | >80,000 | >80,000 | NT |
| 9 | >50,000 | 49,800 ± 20,000 | NT |
| 13 | 10,000 ± 1,800 | NT | NT |
| 14 | 3,050 ± 550 | NT | NT |
| 15 | NT | NT | NT |

Test B. In Vivo Studies

Several representative compounds of the invention were chosen for in vivo studies. The anticancer agent mitomycin C was used as a pharmaceutical control. Drug therapy was started 10 days after inoculation on a daily basis via IP route for 5 consecutive days. The animals were monitored for 3 weeks after start of therapy. The MTD was reached for the control agent mitomycin C but not for compounds 1 or 2.

BALB/c nu/nu 4-week old female mice weighing 18–22 g were obtained from Simonsen, Inc. (Gilroy, Calif.) and maintained in the athymic mouse colony of the University of California (San Diego, Calif.) under pathogen free conditions using HEPA filter hoods. Animals were provided with sterilized food and water ad libitum in groups of 5 in plastic cages vented with polyester fiber filter covers. Clean, sterilized gowns, glove, face masks, and shoe and hood covers were worn by all personnel handling the animals. All studies were conducted in accordance with guidelines of the NIH "Guide for Care and Use of Animals" and approved by the University Institutional Animal Care and Use Committee (Protocol 3-006-2)

The MV522 lung carcinoma line used for xenograft studies was derived as described by Kelner et al. (*Anticancer Res.*, 15: 867–872; 873–878 (1995)) and maintained in antibiotic-free RPMI 1640 (Mediatech, Herndon, Va.) supplemented with 10% fetal bovine serum and 2 mM glutamine in 37° C. humidified carbon dioxide incubator.

Mice were randomized into treatment groups of five animals each for initial studies and groups of 16–20 animals for confirming analogue efficacy. Each animal was earmarked and followed individually throughout the experiments. Mice received s.c. injections of the parental cell line MV522 using 10 million cells/inoculation over the shoulder. Ten days after s.c. implantation of the MV522 cells, when s.c. tumors were approximately 3×3 mm in size, animals received the desired drug and dosage. The effect of the compound on life span was calculated from median survival.

Although MV522 cells kill mice by metastases, primary s.c. tumor growth over the shoulder was monitored starting on the first day of treatment and at weekly intervals thereafter. Tumor size was measured in two perpendicular diameters. Tumor weights were estimated according to the formula w=(width)$^2$×length/2). Relative weights (RW) were calculated to standardized variability in tumor size among test groups at initiation of treatment using the formula RW=Wt/wi, where Wi is the tumor weight for a given animal at beginning of drug treatment and Wt is tumor weight at a subsequent time. Animals were necropsied, and organs were examined for evidence of metastases.

Comparison of survival curves between groups of animals was by the method of Kaplan and Meier. For comparison of relative tumor weights between multiple groups of animals, ordinary ANOVA followed by Tukey-Kramer multiple Comparison post ANOVA analysis was performed (Kelner et al. (*Anticancer Res.*, 15: 867–872; 873–878 (1995)). Probability values (p) less than 0.05 were considered statistically significant.

Data from Test B, for representative compounds of the invention, is shown in Table 2. Data was collected using eight animals in the control studies and four animals in each compound study. Values represent relative tumor weight or Wt/Wi (day ten by definition is 1.0). Drug was administered i.p. on days 10, 11, 12, 13, and 14 (QD×5 days).

TABLE 2

| Compound | Day 17 | Day 24 | Day 31 |
| --- | --- | --- | --- |
| control (saline) | 4.3 ± 0.7 | 7.0 ± 1.3 | 11.8 ± 3.0 |
| 1 (14 mg/kg) | 1.4 ± 0.7 | 7.0 ± 1.3 | 11.8 ± 3.0 |
| 2 (35 mg/kg) | 2.1 ± 0.2 | 3.3 ± 0.3 | 4.0 ± 0.9 |
| 13 (32 mg/kg) | 2.3 ± 0.5 | 4.1 ± 0.8 | 4.7 ± 1.5 |
| 14 (28 mg/kg) | 3.2 ± 0.6 | 4.1 ± 0.8 | 6.0 ± 1.8 |

The data in Tables 1 and 2 shows that representative compounds of the invention are potent cytotoxic and antitumor agents.

The invention will now be illustrated by the following non-limiting Examples, wherein, unless other wise stated: Melting points are uncorrected; $^1$H and $^{13}$C NMR spectra were measured at 300 and 75 MHz; High resolution mass spectra were determined at the University of Minnesota Mass Spectrometry Service Laboratory; Chromatography was performed of silica gel (Davisil 230–425 mesh, Fisher Scientific), with ethyl acetate:hexanes as the eluent; Analytical TLC was carried out on Whatman 4420 222 silica gel plates; and Reactions were routinely monitored by TLC. Synthesis of illudin S, hydroxymethylacylfulvene (HMAF) and fulvene were prepared as previously described (see, e.g., WO 91/04754; WO 94/18151).

EXAMPLES

Example 1

Compound 1 (formula I wherein $R_1$ is hydrogen; $R_2$ is hydroxymethyl; $R_3$ is hydrogen; $R_4$ is methyl; $R_5$ is hydroxy; and $R_6$ is methyl)

To a stirred solution of acylfulvene (6.9 g, 32 mmol) in 7.0 ml of EtOAc, were added 99% Selenium dioxide (1.75 g, 15.8 mmol), and 90% tert-butyl hydroperoxide (6 ml, d 0.901, 60 mmol). The mixture was stirred at room temperature for 24 hr and then partitioned between EtOAc and saturated sodium sulfite (3×3 ml), followed by saturated brine. The organic extract was then dried over $MgSO_4$. After concentration, the crude product was chromatographed to give 922.5 mg of the title compound (12%) as a yellow-orange gum, and 5.8 g of Acylfulvene (84%); $^1$H NMR ($CDCl_3$) δ 0.76 (ddd, 1H), 1.14 (ddd, 1H), 1.27 (ddd, 1H), 1.36 (s, 3H), 1.54 (ddd, 1H), 2.03 (s, 3H), 4.02 (s, 1H), 4.56 (s, 2H), 6.67 (s, 1H), 7.29 (s, 1H); $^{13}$C NMR ($CDCl_3$) δ 197.9, 161.5, 146.0, 140.2, 132.9, 127.0, 119.8, 76.6, 59.9, 37.5, 27.7, 17.0, 14.7, 9.9; MS m/e 232 (M$^+$); UV λ max (EtOH) 327.2 nm (ε 7631).

Example 2

Compound 2 (formula I wherein $R_1$ is hydroxymethyl; $R_2$ is hydroxymethyl; $R_3$ is hydrogen; $R_4$ is methyl; $R_5$ is hydroxy; and $R_6$ is methyl)

Paraformaldehyde (36.3 g) was added to a solution of dilute $H_2SO_4$ (1.5 M, 275 ml), and $Me_2CO$ (300 ml). The mixture was stirred and heated to dissolve all the solid. To the cooled (0° C.) solution compound 1 (922.50 mg, 3.98 mmol) was added, the resulting solution was stirred and allowed to warm to room temperature. After 24 hr, the orange-yellow mixture was extracted with EtOAc (2×300 ml) and the combined extracts washed with saturated $NaHCO_3$ (30 ml), followed by saturated brine. The organic extract was then dried over $MgSO_4$. Removal of solvent and chromatography of the residue on Si gel with EtOAc-hexanes afforded 357.3 mg (34%) of the title compound as a dark yellow-orange gum; $^1$H NMR ($CDCl_3$) δ 0.79 (ddd, 1H), 1.16 (ddd, 1H), 1.26 (ddd, 1H), 1.38 (s, 3H), 1.41 (ddd, 1H), 2.20 (s, 3H), 3.90 (s, 1H), 4.63 (s, 2H), 4.74 (s, 2H), 7.25 (s, 1H), MS m/e 262 (M$^+$); UV λ max (EtOH) 330.0 nm (ε 5011).

Example 3

Compound 3 (formula I wherein $R_1$ is hydrogen; $R_2$ is acetoxymethyl; $R_3$ is hydrogen; $R_4$ is methyl; $R_5$ is hydroxy; and $R_6$ is methyl)

To a stirred solution of compound 1 (76.0 mg, 0.328 mmol) in 2 ml of acetic anhydride at room temperature, anhydrous sodium acetate (126.2 mg, 1.54 mmol) was added. The mixture was stirred at room temperature for 24 hr, filtered to remove the NaOAc. The solution was placed under reduced pressure for 4 hr. The crude product was then partitioned between EtOAc and saturated $NaHCO_3$, followed by saturated brine, and dried over $MgSO_4$. After concentration the residue was chromatographed on Si gel with EtOAc-hexanes to give the title compound (50 mg, 56%) as a yellow gum; $^1$H NMR ($CDCl_3$) δ 0.77 (ddd, 1H), 1.16 (ddd, 1H), 1.34 (ddd, 1H), 1.38 (s, 3H), 1.58 (ddd, 1H), 2.06 (s, 3H), 2.11 (s, 3H), 4.99 (s, 2H), 6.69 (s, 1H), 7.27 (s, 1H); $^{13}$C NMR ($CDCl_3$) δ 197.9, 170.8, 163.6, 140.5, 140.0, 132.8, 126.7, 121.9, 76.7, 61.3, 37.9, 27.8, 20.9, 17.3, 15.3, 10.3.

Example 4

Compound 4 (formula I wherein $R_1$ is acetoxymethyl; $R_2$ is hydroxymethyl; $R_3$ is hydrogen; $R_4$ is methyl; $R_5$ is hydroxy; and $R_6$ is methyl)

To a stirred solution of compound 10 (430 mg, 1.49 mmol) in 3 ml of EtOAc, 99% selenium dioxide (186 mg, 1.67 mmol) was added, followed by 90% tert-butyl hydroperoxide (0.40 ml, d 0.901, 4.0 mmol). The mixture was let stir at room temperature for 4 days, and then partitioned between EtOAc and saturated sodium sulfite (3×3 ml), followed by saturated brine, and dried over magnesium sulfate. After concentration the crude product was chromatographed to give the title compound (8.5 mg, 2%) as a yellow gum; $^1$H NMR ($CDCl_3$) δ 0.79 (ddd, 1H), 1.17 (ddd, 1H), 1.39 (s, 3H), 1.43 (ddd, 1H), 1.52 (ddd, 1H), 2.09 (s, 3H), 2.14 (s, 3H), 3.93 (s, 1H), 4.65 (q, 2H), 5.21 (q, 2H), 7.32 (s, 1H); MS m/e 304 (M_+); UV λ max (EtOH) 330.6 nm (ε 5950).

The intermediate compound 10 was prepared as follows.

a. Compound 10. Anhydrous sodium acetate was added to a stirred solution of HMAF (1.4 g, 5.7 mmol) in acetic anhydride (6 mL) at room temperature. After 18 hours, the mixture was filtered and the resulting solution was placed under reduced pressure for 4 hours. The resulting material was partitioned between ethyl acetate and saturated aqueous sodium bicarbonate, followed by brine, and the resulting ethyl acetate solution was dried over magnesium sulfate. The solution was concentrated and purified by chromatography on silica gel with ethyl acetate:hexanes as the eluent to give compound 10 (1.4 g, 85%) as a yellow-orange gum; $^1$H NMR (CDCl$_3$) δ 0.74 (ddd, 1H), 1.11 (ddd, 1H), 1.36 (s, 3H), 1.51 (ddd, 1H), 2.04 (s, 3H), 2.09 (s, 3H), 2.17 (s, 3H), 3.90 (s, 1H), 5.10 (s, 2h), 7.11 (s, 1H).

Example 5

Compound 5 (formula I wherein $R_1$ is acetoxymethyl; $R_2$ is acetoxymethyl; $R_3$ is hydrogen; $R_4$ is methyl; $R_5$ is hydroxy; and $R_6$ is methyl)

To a stirred solution of compound 4 (2 mg, 0.0066 mmol) in 15 μl of CH$_2$Cl$_2$ and 135 μl of acetic anhydride, anhydrous NaOAc (3.1 mg, 0.038 mmol) was added. The reaction was let stir at room temperature for 4 hr, filtered to remove the NaOAc. The mixture was placed under reduced pressure to remove the acetic anhydride. The crude product was then partitioned between EtOAc and saturated NaHCO$_3$, followed by saturated brine, and dried over MgSO$_4$. After concentration the residue was chromatographed on Si gel with EtOAc-hexanes to give the title compound (0.9 mg, 40%) as a yellow gum. $^1$H NMR (CDCl$_3$) δ 0.79 (ddd, 1H), 1.15 (ddd, 1H), 1.39 (s, 3H), 1.40 (ddd, 1H), 1.58 (ddd, 1H), 2.09 (s, 3H), 2.093 (s, 3H), 2.10 (s, 3H), 3.89 (s, 1H), 5.08 (s, 2H), 5.17 (s, 2H), 7.25 (s, 1H); MS m/e 346 (M$^+$); UV λ max (EtOH) 332.1 nm (ε 8378).

Example 6

Compound 6 (formula I wherein $R_1$ is hydroxymethyl; $R_2$ is acetoxymethyl; $R_3$ is hydrogen; $R_4$ is methyl; $R_5$ is hydroxy; and $R_6$ is methyl)

To a stirred solution of compound 2 (76.0 mg, 0.290 mmol) in 1.5 ml of acetic anhydride, anhydrous NaOAc (45.3 mg, 0.552 mmol) was added. The reaction mixture was stirred at room temperature for 75 min then, filtered to remove the NaOAc. The mixture was partitioned between EtOAc and saturated NaHCO$_3$, followed by saturated brine, and dried over MgSO$_4$. The extract was concentrated under reduced pressure and the residue was chromatographed on Si gel with EtOAc-hexanes to give compound 4 (6.9 mg) as a yellow gum, compound 2 (10.0 mg) as a yellow orange gum, 3 minor products including compound 5, and the title compound (10.0 mg, 11.3%) as a yellow gum; $^1$H NMR (CDCl$_3$) δ 0.81 (ddd, 1H), 1.17 (ddd, 1H), 1.38 (s, 3H), 1.60 (ddd, 1H), 2.06 (s, 3H), 2.24 (s, 3H), 3.89 (s, 1H), 4.74 (m, 2H), 5.03 (m, 2H), 7.23 (1H); MS m/e 304 (M$^+$); UV λ max (EtOH) 331.3 nm (ε 5921).

Example 7

Compound 7 (formula I wherein $R_1$ is hydrogen; $R_2$ is methoxymethyl; $R_3$ is hydrogen; $R_4$ is methyl; $R_5$ is hydroxy; and $R_6$ is methyl)

To a stirred solution of compound 1 (300 mg, 1.29 mmol) in 10 ml of CH$_3$CN, 1 ml of CH$_3$I, and Ag$_2$O (110 mg, 0.475 mmol) were added. The mixture was stirred at room temperature for 3 days, then filtered and concentrated. The residue was chromatographed on Si gel with EtOAc-hexanes giving compound 1 (133 mg) and the title compound (53 mg, 17%) as a dark orange gum; $^1$H NMR (CDCl$_3$) δ 0.76 (ddd, 1H), 1.13 (ddd, 1H), 1.34 (ddd, 1H), 1.38 (s, 3H), 2.05 (s, 3H), 3.41 (s, 3H), 3.96 (s, 1H), 4.35 (s, 2H), 6.66 (s, 1H), 7.28 (s, 1H); $^{13}$C NMR (CDCl$_3$) δ 197.8, 161.8, 143.3, 140.2, 133.1, 126.7, 120.9, 76.6, 69.6, 58.3, 37.6, 27.8, 17.1, 14.9, 10.0.

Example 8

Compound 8 (formula I wherein $R_1$ is methoxymethyl; $R_2$ is hydroxymethyl; $R_3$ is hydrogen; $R_4$ is methyl; $R_5$ is hydroxy; and $R_6$ is methyl)

To a stirred solution of compound 11 (830 mg, 3.19 mmol) in 10 ml of EtOAc, 99% selenium dioxide (150 mg, 1.35 mmol) was added, followed by 90% tert-butyl hydroperoxide (1 ml, d 0.901, 10.0 mmol). The reaction mixture was stirred at room temperature for 5 days, partitioned between diethyl ether and saturated sodium sulfite, followed by saturated brine, and dried over MgSO$_4$. After concentration the crude material was chromatographed to give the title compound. (47.2 mg, 5%) as a dark orange gum. $^1$H NMR (CDCl$_3$) δ 0.74 (ddd, 1H), 1.08 (ddd, 1H), 1.32 (s, 3H), 1.33 (ddd, 1H), 1.47 (ddd, 1H), 2.08 (s, 3H), 3.14 (br s, 1H), 3.35 (s, 3H), 4.41 (q, 2H), 4.51 (br s, 2H), 7.28 (s, 1H).

a. Compound 11. The intermediate compound 11 (formula I wherein $R_1$ is methoxymethyl; $R_2$ is methyl; $R_3$ is hydrogen; $R_4$ is methyl; $R_5$ is hydroxy; and $R_6$ is methyl) was prepared as follows.

To a stirred solution of HMAF (320 mg, 1.3 mmol) in 3 ml Me$_2$CO, MeOH (3 ml), and dilute H$_2$SO$_4$ (1M, 3 ml) were added. The reaction mixture was stirred at room temperature for 24 hours and extracted with diethyl ether. The combined extracts were washed (saturated NaHCO$_3$, followed by brine), and dried over MgSO$_4$. After concentration the residue was chromatographed on Si gel with EtOAc-hexanes affording compound 50 (290 mg, 86%) as a dark orange gum; $^1$H NMR (CDCl$_3$) δ 0.62 (ddd, 1H), 0.98 (ddd, 1H), 1.24 (ddd, 1H), 1.27 (s, 3H), 1.37 (ddd, 1H), 2.00 (s, 3H), 2.04 (s, 3H), 3.26 (s, 3H), 3.91 (br s, 1H), 4.29 (q, 2H), 7.0 (s, 1H); $^{13}$C NMR (CDCl$_3$) δ 197.6, 159.7, 142.6, 138.8, 134.3, 129.7, 126.6, 75.9, 65.3, 57.3, 37.3, 27.3, 15.7, 13.9, 12.9, 9.1.

Example 9

Compound 9 (formula I wherein $R_1$ is methoxymethyl; $R_2$ is methoxymethyl; $R_3$ is hydrogen; $R_4$ is methyl; $R_5$ is hydroxy; and $R_6$ is methyl)

To a stirred solution of compound 8 (240 mg, 0.87 mmol) in 15 ml of CH$_3$CN, 1.5 ml CH$_3$I, and Ag$_2$O (150 mg, 0.647 mmol) were added. The reaction mixture was stirred at room temperature for 48 hr, filtered an concentrated. The residue was chromatographed on Si gel with EtOAc-hexanes to give the title compound (25 mg, 10%) as a yellow-orange gum;

¹H NMR (CDCl₃) δ 0.76 (ddd, 1H), 1.11 (ddd, 1H), 1.37 (s, 3H), 1.40 (ddd, 1H), 1.53 (ddd, 1H), 2.13 (s, 3H), 3.36 (s, 3H), 3.38 (s, 3H), 3.91 (s, 1H), 4.37 (q, 2H), 4.43 (q, 2H), 7.27 (s, 1H), $^{13}$C NMR (CDCl₃) δ 198.0, 163.4, 142.8, 139.1, 132.6, 132.0, 127.2, 76.6, 67.2, 65.5, 58.3, 57.8, 38.1, 27.5, 16.3, 14.8, 9.8.

Example 10

Compound 12 (formula I wherein R₁ is —CH₂-[sulfur-linked-cysteine]; R₂ is methyl; R₃ is hydrogen; R₄ is Methyl; R₅ is hydroxy; and R₆ is methyl)

To a solution of HMAF in acetone and 1M H₂SO₄ (1:1) was added one equivalent of cysteine. The mixture was stirred at room temperature overnight. A large amount of EtOAc was added and the water was removed by adding MgSO₄. Solid NaHCO₃ was also added in order to neutralize the sulfuric acid. The solution was filtered, concentrated, and chromatographed, to give compound 102 as a yellow gum: ¹H NMR (CDCl₃) δ 0.78 (m, 1H), 0.89 (m, 1H), 1.06 (m, 1H), 1.31 (s, 3H), 1.43 (m, 1H), 2.15 (s, 3H), 2.21 (s, 3H), 2.91–4.02 (m, 8H), 7.04 (s, 1H).

Example 11

Compound 13 (formula I wherein R₁ is —CH₂-[sulfur-linked —N-acylcysteine]; R₂ is methyl; R₃ is hydrogen; R₄ is methyl; R₅ is hydroxy; and R₆ is methyl).

To a solution of HMAF (36 mg, 0.146 mmol) in 1:1 1M H₂SO₄/acetone (3 mL) was added N-acetyl cysteine (22.4 mg, 0.137 mmol) at room temperature. The mixture was stirred for 22 hours and was extracted with ethyl acetate. The organic extracts were washed with saturated NaHCO₃ and saline respectively. The solution was dried over MgSO₄. After concentration, the crude product was chromatographed (adding 2–5% acetic acid to the normal solvent mixture, ethyl acetate and hexanes) to give 45.5 mg of compound 103 (85% yield) as a yellow gum; ¹H NMR (CDCl₃) δ 0.72 (m, 1H), 1.09 (m, 1H), 1.23 (m, 1H), 1.36 (s, 3H), 1.47 (m, 1H), 2.07 (s, 3H), 2.10 (s, 3H), 2.13 (s, 3H), 2.97 (m, 1H), 3.14 (m, 1H), 3.82 (dd, 3.82), 4.80 (m, 2H), 6.56 (d, J=7.2 Hz), 7.10 (s, 1H); MS m/e 391 (M⁺), 373, 229, 185; HRMS for C₂₀H₂₅NO₅S calcd 391.1455, found 391.1452.

Example 12

Compound 14 (formula I Wherein R₁ is (S)-2-[(R)-α-methylbenzyl-aminocarbonyl]-2-(acylamino)ethylthiomethyl; R₂ is Methyl; R₃ is Hydrogen; R₄ is methyl; R₅ is hydroxy; and R₆ is methyl).

To a solution of compound 13 (40 mg, 0.102 mmol) in methylene chloride (1 mL) was added N-hydroxybenzotriazole (20 mg, 0.132 mmol), N,N-diisopropylcarbodiimide (20 μL, 0.12 mmol) and (d)-(+)-α-methyl benzylamine (12 μL, 0.093 mmol). The mixture was stirred for 1.5 hours at room temperature. The mixture was partitioned between EtOAc and water. The organic extract was dried over MgSO₄. After concentration the crude product was chromatographed to give 33.6 mg of compound 14 (73%) as a yellow gum; ¹H NMR (CDCl₃) δ 0.70 (m, 1H), 1.07 (m, 1H), 1.29 (m, 1H), 1.35 (s, 3H), 1.48 (d, J=6.9 Hz, 3H), 1.51 (m, 1H), 1.93 (s, 3H), 2.09 (s, 3H), 2.10 (s, 3H), 2.91 (m, 2H), 3.84 (dd, 2H), 4.61 (m, 1H), 5.03 (m, 1H), 6.64 (d, J=7.8 Hz, 1H), 7.07 (s, 1H), 7.26 (m, 5H); ¹³C NMR (CDCl₃) δ 197.5, 170.4, 169.2, 159.7, 142.6, 142.0, 138.3, 134.9, 129.8, 128.7, 127.4, 126.4, 125.9, 77.4, 52.5, 49.3, 37.7, 34.4, 29.8, 27.6, 23.1, 22.1, 16.3, 14.3, 13.1, 9.5; HRMS for C₂₈H₃₄N₂O₄S calcd 494.2241, found 494.2225.

Example 13

Compound 15 (formula I wherein R₁ is (R)-2-[(R)-α-methylbenzyl-aminocarbonyl]-2-(acylamino)ethylthiomethyl; R₂ is methyl; R₃ is hydrogen; R₄ is methyl; R₅ is hydroxy; and R₆ is methyl).

The chromatography from Example 12 also provided 5.3 mg of compound 15 (13%) as a yellow gum; ¹H NMR (CDCl₃) δ 0.70 (m, 1H), 1.07 (m, 1H), 1.32 (m, 1H), 1.34 (s, 3H), 1.45 (m, 1H), 1.48 (d, J=6.9 Hz, 3H), 2.03 (s, 3H), 2.05 (s, 6H), 2.76 (m, 1H), 2.87 (m, 1H), 3.73 (dd, 2H), 4.50 (m, 1H), 5.03 (m, 1H), 6.46 (d, J=7.5 Hz, 1H), 6.77 (d, J=7.8 Hz, 1H), 7.05 (s, 1H), 7.31 (m, 5H); HRMS for C₂₈H₃₄N₂O₄S calcd 494.2241, found 494.2238.

Example 14

Compound 16 (formula I wherein R₁ is —CH₂-[sulfur-linked-glutathione]; R₂ is methyl; R₃ is hydrogen; R₄ is methyl; R₅ is hydroxy; and R₆ is methyl).

Using a procedure similar to that described in Example 10 except replacing the cysteine used therein with glutathione, compound 16 was prepared.

Example 15

General procedure for the synthesis of compounds wherein R₁ is —CH₂-[sulfur-linked-cysteine]-peptide, —CH₂-[sulfur-linked-cysteine]-(amino acid), —CH₂-[sulfur-linked-N-acylcysteine]-peptide, or —CH₂-[sulfur-linked-N-acylcysteine]-(amino acid).

Using solid phase peptide synthesis techniques, which are well known in the art, the amino acids Leu, Phe and Gly were combined to give the following resin bound tripeptides and dipeptides.

```
-Leu-Leu-Leu    -Leu-Leu-Phe    -Leu-Leu-Gly
-Leu-Phe-Leu    -Leu-Phe-Phe    -Leu-Phe-Gly
-Leu-Gly-Leu    -Leu-Gly-Phe    -Leu-Gly-Gly
-Phe-Leu-Leu    -Leu-Leu-Phe    -Phe-Leu-Gly
-Phe-Phe-Leu    -Phe-Phe-Phe    -Phe-Phe-Gly
-Phe-Gly-Leu    -Phe-Gly-Phe    -Phe-Gly-Gly
-Gly-Leu-Leu    -Gly-Leu-Phe    -Gly-Leu-Gly
-Gly-Phe-Leu    -Gly-Phe-Phe    -Gly-Phe-Gly
-Gly-Gly-Leu    -Gly-Gly-Phe    -Gly-Gly-Gly
-Leu-Leu        -Leu-Phe        -Leu-Gly
-Phe-Leu        -Phe-Phe        -Phe-Gly
-Gly-Leu        -Gly-Phe        -Gly-Gly
```

A rink acid resin having the following structure, wherein "P" represents a polystyrene divinylbenzene resin, was used in the solid phase reactions.

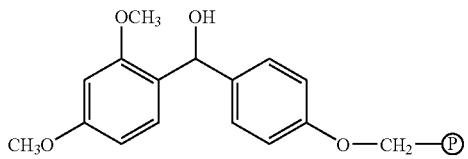

The first N-(9-fluorenylmethoxycarbonyl)-protected amino acid was coupled to the resin via a bond formation between its C-terminus and the hydroxyl group of the resin using DIPC (Diisopropylcarbodiimide)/DMAP (4-Dimethylaminopyridine). The percent yield was calculated after the coupling, and if it was below 90%, the coupling was repeated until the percent yield exceeded 90%. The N-(9-fluorenylmethoxycarbonyl)-group (Fmoc-group) of the first amino acid was removed by treatment with 20% piperidine in 1-Methyl-2-Pyrrolidinone (NMP). A Kaiser's Test was performed to check the result of the deprotection. The three Kaiser's reagents (Ninhydrin, Phenol and Potassium Cyanide) were added to an aliquot of resin sample to yield a light yellowish solution. The mixture was heated at 100° C. for 3 minutes, and if the solution turned dark purple (positive result), the Fmoc-group was considered to have been removed. The next amino acid was coupled by peptide bond formation using DIPC/HOBT(1-Hydroxy-Benzotriazole). NMP was used as the solvent for deprotection, coupling, and washing and, dichloromethane was used as the drying reagent. Another Kaiser's test was then performed, with no color change (negative result) indicating that the coupling was successful. The coupling reaction was repeated to add additional amino acids. Compound 13 was coupled to the final resin bound amino acid or peptide using dichloromethane as the solvent. NMP was not used as the solvent for the coupling reaction with compound 13, because NMP has been shown to cause inversion of the chiral center in cysteine, yielding a racemic mixture. Additionally, HOBT was not used in the coupling reaction with compound 13, because it may also contribute to the formation of a mixture of products. The cleavage of the resin from the peptide was achieved by treatment with 10% acetic acid in dichloromethane. The products were tested by UV and Mass Spectroscopy. HMAF gives two maximal UV absorbances at about 210 nm and 330 nm, so the presence of products was confirmed by the presence of these two absorbances. Mass Spectroscopy was also used to confirm the presence of the desired products.

Using this general procedure, compound 13 was coupled with the 36 tri- and di-peptides shown above, and with the individual amino acids Leu, Phe and Gly, to give a total of 39 compounds of the invention. The N-acetyl group of these 39 compounds can also be removed using conditions similar to those described in Example 11 to give an additional 39 compounds of the invention. Accordingly, in a compound of formula I, $R_x$ may preferably represent Leu, Phe, Gly, or any of the 36 tri- and di-peptides shown above.

Example 16

Compound 17 (formula I wherein $R_1$ is (S)-2-(2-carboxypyrrolidin-1-ylcarbonyl)propylthiomethyl; $R_2$ is methyl; $R_3$ is hydrogen; $R_4$ is methyl; $R_5$ is hydroxy; and $R_6$ is methyl).

Using a procedure similar to that described in Example 10 except replacing the cysteine used therein with 1-(3-mercapto-2-methyl-1-oxopropyl)-L-proline (captopril), compound 17 was prepared.

Example 17

Compound 18 (formula II wherein $R_2$ is methyl; $R_3$ is hydrogen; $R_4$ is methyl; $R_5$ is hydroxy; $R_6$ is methyl, and $R_7$ is hydroxymethyl).

Illudin S (178.5 mg) was dissolved in acetic anhydride (2.0 mL) and sodium acetate (96 mg) was added. After 24 hours a mixture of mono and diacetate was obtained. The monoacetate (171 mg) was dissolved in dichloromethane and pyridinium dichromate (695 mg) was added. The mixture was stirred at room temperature for 21 hours. Work-up yielded dehydroilludin S monoacetate (118 mg), which was dissoved in acetone (5 mL) and 1M sulfuric acid (3 mL) for 12 hours to give compound 18 (66 mg);$^1$H NMR (CDCl$_3$) δ 0.63 (1H), 1.13 (1H), 1.23 (4H), 1.38 (4H), 2.05 (3H), 3.62 (1H), 3.76 (1H), 6.82 (1H).

Example 18

The following illustrate representative pharmaceutical dosage forms, containing a compound of formula I or II ('Compound X'), for therapeutic or prophylactic use in humans.

| (I) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

-continued

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A compound of formula I:

wherein
$R_1$ is $CH_2$-(sulfur-linked-cysteine)-$R_x$ or $CH_2$-(sulfur-linked-N-acylcysteine)-$R_x$ wherein $R_x$ is an amino acid or a peptide comprising 2 to 24 amino acids;
$R_2$ is carboxy, $(C_1-C_6)$alkanoyl, $(C_1-C_6)$alkoxycarbonyl, halo$(C_1-C_6)$alkyl, —C(=O)$NR_dR_e$, a saccharide, an amino acid, a peptide, or $(C_1-C_6)$alkyl substituted by 1 or 2 hydroxy, $(C_1-C_6)$alkoxy, $(C_1-C_6)$alkanoyloxy, carboxy, amino acids, peptides, saccharides, or —C(=O)$NR_dR_e$;
$R_3$ is hydrogen, $(C_1-C_6)$alkyl, $(C_1-C_6)$alkoxy, $(C_1-C_6)$alkylthio, aryl, heteroaryl, aryloxy, or heteroaryloxy;
$R_4$ is hydrogen or $(C_1-C_6)$alkyl; and $R_5$ is hydroxy, $(C_1-C_6)$alkoxy, or $(C_1-C_6)$alkanoyloxy; or $R_4$ and $R_5$ taken together are ethylenedioxy;
$R_6$ is hydrogen, carboxy, $(C_1-C_6)$alkanoyl, $(C_1-C_6)$alkoxycarbonyl, halo$(C_1-C_6)$alkyl, —C(=O)$NR_fR_g$, a saccharide, an amino acid, a peptide, or $(C_1-C_6)$alkyl optionally substituted by 1 or 2 hydroxy, $(C_1-C_6)$alkoxy, $(C_1-C_6)$alkanoyloxy, carboxy, amino acids, peptides, saccharides, or —C(=O)$NR_fR_g$;
$R_d$, $R_e$, $R_f$ and $R_g$ are each independently hydrogen, $(C_1-C_6)$alkyl, $(C_1-C_6)$alkanoyl, phenyl or benzyl; or $R_d$ and $R_e$, or $R_f$ and $R_g$, together with the nitrogen to which they are attached, are pyrrolidino, piperidino, or morpholino;
wherein any aryl, heteroaryl, aryloxy, or heteroaryloxy of $R_3$ may optionally be substituted by 1, 2, or 3 $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, hydroxy$(C_1-C_6)$alkyl, halo$(C_1-C_6)$alkyl, hydroxy, halo, carboxy, mercapto, nitro, or —N($R_h$)($R_j$); wherein each $R_h$ and $R_j$ is independently hydrogen, $(C_1-C_6)$alkyl, $(C_1-C_6)$alkanoyl, phenyl or benzyl; or $R_h$ and $R_j$ together with the nitrogen to which they are attached are pyrrolidino, piperidino, or morpholino;
or a pharmaceutically acceptable salt thereof.

2. The compound of claim 1 wherein $R_1$ is $CH_2$-(sulfur-linked-cysteine)-$R_x$.

3. The compound of claim 1 wherein $R_1$ is $CH_2$-(sulfur-linked-N-acylcysteine)-$R_x$.

4. The compound of claim 1 wherein $R_x$ is -Leu-Leu-Leu, -Leu-Phe-Leu, -Leu-Gly-Leu, -Leu-Leu-Phe, -Leu-Phe-Phe, -Leu-Gly-Phe, -Leu-Leu-Gly, -Leu-Phe-Gly, -Leu-Gly-Gly, -Phe-Leu-Leu, -Phe-Phe-Leu, -Phe-Gly-Leu, -Gly-Leu-Leu, -Gly-Phe-Leu, -Gly-Gly-Leu, -Leu-Leu, -Phe-Leu, -Gly-Leu, -Leu-Leu-Phe, -Phe-Phe-Phe, -Phe-Gly-Phe, -Gly-Leu-Phe, -Gly-Phe-Phe, -Gly-Gly-Phe, -Leu-Phe, -Phe-Phe, -Gly-Phe, -Phe-Leu-Gly, -Phe-Phe-Gly, -Phe-Gly-Gly, -Phe-Leu-Gly, -Gly-Phe-Gly, -Gly-Gly-Gly, -Leu-Gly, -Phe-Gly, or -Gly-Gly.

5. The compound of claim 1 wherein $R_x$ is -Gly-Gly-Leu, -Gly-Leu-Leu, -Gly-Phe-Leu, -Leu-Gly-Leu, -Leu-Leu-Leu, -Leu-Phe-Leu, -Phe-Gly-Leu, -Phe-Leu-Leu, -Phe-Phe-Leu, -Leu-Leu, -Phe-Leu, or -Gly-Leu.

6. The compound of claim 1 wherein $R_x$ is -Gly-Gly-Phe, -Gly-Leu-Phe, -Gly-Phe-Phe, -Leu-Gly-Phe, -Leu-Leu-Phe, -Leu-Phe-Phe, -Phe-Gly-Phe, -Phe-Leu-Phe, -Phe-Phe-Phe, -Leu-Phe, -Phe-Phe, or -Gly-Phe.

7. The compound of claim 1 wherein $R_x$ is -Gly-Gly-Gly, -Gly-Phe-Gly, -Leu-Gly-Gly, -Leu-Leu-Gly, -Leu-Phe-Gly, -Phe-Gly-Gly, -Phe-Leu-Gly, -Phe-Phe-Gly, -Leu-Gly, -Phe-Gly, or -Gly-Gly.

8. The compound of claim 1 wherein $R_x$ is -Leu-Leu, -Phe-Leu, -Gly-Leu, -Leu-Phe, -Phe-Phe, -Gly-Phe, -Leu-Gly, -Phe-Gly, or -Gly-Gly.

9. The compound of claim 1 wherein $R_x$ is -Leu-Leu-Leu.

10. The compound of claim 1 wherein $R_x$ is -Leu-Leu-Phe.

11. The compound of claim 1 wherein $R_x$ is -Leu-Gly-Phe.

12. The compound of claim 1 wherein $R_x$ is -Phe-Gly-Leu.

13. The compound of claim 1 wherein $R_2$ is carboxy, $(C_1-C_6)$alkanoyl, $(C_1-C_6)$alkoxycarbonyl, halo$(C_1-C_6)$alkyl, or —C(=O)$NR_dR_e$.

14. The compound of claim 1 wherein $R_2$ is $(C_1-C_6)$alkyl substituted by 1 or 2 hydroxy, $(C_1-C_6)$alkoxy, $(C_1-C_6)$alkanoyloxy, carboxy, amino acids, peptides, saccharides, or —C(=O)$NR_dR_e$.

15. The compound of claim 1 wherein $R_3$ is $(C_1-C_6)$alkyl, $(C_1-C_6)$alkoxy, or $(C_1-C_6)$alkylthio.

16. The compound of claim 1 wherein $R_3$ is aryl, heteroaryl, aryloxy, or heteroaryloxy.

17. The compound of claim 1 wherein $R_4$ is hydrogen or $(C_1-C_6)$alkyl; and $R_5$ is hydroxy, $(C_1-C_6)$alkoxy, or $(C_1-C_6)$alkanoyloxy.

18. The compound of claim 1 wherein $R_4$ and $R_5$ taken together are ethylenedioxy.

19. The compound of claim 1 wherein $R_6$ is hydrogen, carboxy, $(C_1-C_6)$alkanoyl, $(C_1-C_6)$alkoxycarbonyl, halo $(C_1-C_6)$alkyl, —C(=O)$NR_fR_g$, or $(C_1-C_6)$alkyl optionally substituted by 1 or 2 hydroxy, $(C_1-C_6)$alkoxy, $(C_1-C_6)$alkanoyloxy, carboxy, or —C(=O)$NR_fR_g$.

20. A pharmaceutical composition comprising one or more compounds of claim 1 and a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 7,141,603 B2 | Page 1 of 1 |
| APPLICATION NO. | : 11/151013 | |
| DATED | : November 28, 2006 | |
| INVENTOR(S) | : McMorris et al. | |

It is certified that error appears in the above-identified patent and that said Letters Patent is hereby corrected as shown below:

In column 2, line 57, delete "$R_e$or" and insert -- $R_e$, or --, therefor.

In column 3, line 36, delete "–N($R_h$($R_j$)" and insert -- –N($R_h$)($R_j$) --, therefor.

In column 4, lines 20-21, delete "–(CH$_2$)$_p$–O–(CH$_2$)$_q$" and insert -- –(CH$_2$)$_p$–O–(CH$_2$)$_q$– --, therefor.

In column 5, line 21, delete "R" and insert -- $R_5$ --, therefor.

In column 9, line 17, after "CH$_2$CO$_2$(C$_1$–C$_4$)alkyl" insert -- , --.

In column 11, line 38, delete "RP" and insert -- $R_5$ --, therefor.

In column 16, line 3, delete "mean±1" and insert -- mean ± 1 --, therefor.

In column 19, line 2, delete "M$_+$" and insert -- M$^+$ --, therefor.

In column 21, line 12, delete "Methyl" and insert -- methyl --, therefor.

In column 21, line 50, delete "Wherein" and insert -- wherein --, therefor.

In column 21, line 52, delete "Methyl" and insert -- methyl --, therefor.

In column 21, line 52, delete "Hydrogen" and insert -- hydrogen --, therefor.

Signed and Sealed this

Twenty-fourth Day of June, 2008

JON W. DUDAS
*Director of the United States Patent and Trademark Office*